United States Patent [19]

Almquist et al.

[11] Patent Number: 5,268,361
[45] Date of Patent: Dec. 7, 1993

[54] HYDROXYAZIDO DERIVATIVES AND RELATED COMPOUNDS AS RENIN INHIBITORS

[75] Inventors: Ronald G. Almquist, Palo Alto, Calif.; Atsuro Nakazato, Saitama, Japan

[73] Assignee: SRI International, Menlo Park, Calif.

[21] Appl. No.: 712,311

[22] Filed: Jun. 7, 1991

[51] Int. Cl.$^5$ .................. A61K 37/02; C07K 5/06
[52] U.S. Cl. ...................... 514/19; 514/18; 530/330; 530/331
[58] Field of Search .............. 530/330, 331; 514/18, 514/19

[56] References Cited

FOREIGN PATENT DOCUMENTS 416373 3/1991 European Pat. Off. .

OTHER PUBLICATIONS

Chemical Abstracts, vol. 111, No. 7, Aug. 14, 1989, Abstract 111:58354v.

Chemical Abstracts, vol. 115, No. 7, Aug. 19, 1991, Abstract 115:72226u

*Primary Examiner*—Ronald W. Griffin
*Attorney, Agent, or Firm*—Dianne E. Reed

[57] ABSTRACT

Novel compounds useful as renin inhibitors are provided. The compounds are hydroxyazido derivatives having the structural formula

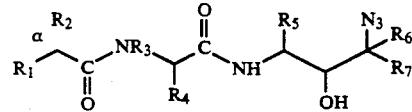

wherein the substituents $R_1$ through $R_7$ are as defined herein. Analogs of these compounds which are ketozaido derivatives are also provided. Additionally disclosed re methods for using the novel compounds to treat hypertension, and pharmaceutical compositions containing the compounds. Of particular interest are formulations for oral administration.

4 Claims, No Drawings

HYDROXYAZIDO DERIVATIVES AND RELATED COMPOUNDS AS RENIN INHIBITORS

TECHNICAL FIELD

This invention relates generally to renin inhibitors, and more particularly relates to novel organic compounds which are useful as renin inhibitors, to pharmaceutical compositions containing those compounds, and to methods of using the compounds to treat hypertension.

BACKGROUND

Renin is a critical protein in the angiotensin system which control vasoconstriction/dilation, as it is the first and rate-limiting enzyme in the formation of the vasoactive octapeptide known as angiotensin II. Angiotensin II is known to be a potent pressor substance, i.e., a substance which can induce a significant increase in blood pressure, and is believed to act by causing the constriction of blood vessels and the release of the sodium-retaining hormone aldosterone from the adrenal gland. Renin is known to be active in in vivo in specifically cleaving angiotensinogen, giving rise to the decapeptide intermediate angiotensin I, which is in turn converted (via "converting enzyme") to angiotensin II.

The renin-angiotensinogen system has thus been implicated as a causative factor in certain forms of hypertension and congestive heart failure. The various features of the foregoing angiotensin system offer a number of opportunities for the targeting of therapeutic drugs. Various approaches have, in fact, been tried. A large family of drugs, β-adrenergic inhibitors (also known as β-blockers) have been used extensively, and are known to act, at least in part, by inhibiting renin secretion from the juxtaglomerular cells of the kidney. Angiotensin converting enzyme ("ACE") inhibitors have also been used to inhibit conversion of angiotensin I to angiotensin II; examples of ACE inhibitor drugs include captopril and enalapril. In addition, drugs which interfere directly with angiotensin II action have been developed, including, for example, saralasin, which is a competitive inhibitor of angiotensin II binding.

Many of the currently available drugs for alleviating the adverse effects of the functioning of the renin-angiotensinogen system are unsatisfactory for one reason or another. Efficacy of the drugs is often unpredictable, and unwanted side effects, due to a multiplicity of biological activities in addition to that intended, are frequent. Also, many drugs intended to reduce hypertension cannot be administered orally. This is particularly true with renin inhibitors, many of which have been shown to be active in lowering blood pressure in both animals and humans when administered intravenously or intramuscularly (see, e.g., E. Haber, *Hypertension and the Angiotensin System: Therapeutic Approaches*, Raven Press 133-145 (1984), and J. P. Gagnol, et al., *Abstracts of the International Society of Hypertension*, 10:376) (1984), but are not orally active.

Accordingly, the present invention is directed to a novel class of organic compounds which in large part overcome the aforementioned disadvantages of the prior art. In particular, a new class of orally active renin inhibitors is provided.

PERTINENT ART

The following references describe organic compounds which are stated to be useful as renin inhibitors: U.S. Pat. Nos. 4,645,759, 4,652,551, 4,680,284, 4,725,583, 4,725,584 and 4,826,815 to Luly et al.; U.S. Pat. Nos. 4,837,204 and 4,857,507 to Rosenberg et al.; U.S. Pat. No. 4,826,958 to Sham; and European Patent Publication No. 297815, inventor Hoover. U.S. Pat. No. 4,927,807 to Stein et al. describes a method and compositions for treating glaucoma, and also sets forth a novel class of renin inhibiting compounds.

S. H. Rosenberg et al., *J. Med. Chem.* 32:1371-1378 (1989), describes preparation of azidomethyl-substituted 1,2- and 1,3-diols and their potential use as renin inhibitors. The authors found oral absorption of the compounds to be very low and concluded that this was the result of extensive liver extraction.

M. Bursztyn et al., *J. Cardiovascular Pharmacol.* 15:493-500 (1990) describe tests done on "A-64662" (also known as "enalkiren"), a renin inhibitor encompassed generically within the disclosure and claims of U.S. Pat. No. 4,927,807 to Stein et al., cited above. H. D. Kleinert et al., *Hypertension* 11:613-619 (1988), A. Delabays et al., *Hypertension* 13:941-947 (1989), and H. N. Glassman et al., *J. Cardiovascular Pharmacol.* 16:S76-S81 (1990) relate to studies conducted on the same compound. The compound was found to be orally active in animals.

A. K. L. Fung et al., "Modified A-64662 analogues as Renin Inhibitors and Anti-Glaucoma Agents", poster #134 at the Boston ACS Meeting, Apr. 23-27, 1990, and S. H. Rosenberg et al., "Development of a Highly Potent, Water Soluble Renin Inhibitor with a Prolonged Duration of Action, poster #132 at the Boston ACS Meeting, Apr. 23-27, 1990, describe enalkiren analogues containing an azide group.

A. H. van den Meiracker et al., *Brit. Med. J.* 301:205-210 (1990), describe an orally active renin inhibitor which is structurally somewhat similar to enalkiren.

SUMMARY OF THE INVENTION

Accordingly, it is a primary object of the invention to provide a novel class of organic compounds which are therapeutically effective, orally active renin inhibitors.

It is another object of the invention to provide pharmaceutical compositions containing the novel compounds.

It is still another object of the invention to provide methods of using the novel compounds to treat hypertension in an individual in need of such treatment.

Additional objects, advantages and novel features of the invention will be set forth in part in the description which follows, and in part will become apparent to those skilled in the art upon examination of the following, or may be learned by practice of the invention.

In its broadest aspect, the invention is directed to novel organic compounds having the structural formula

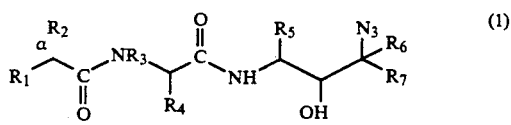

wherein α represents an optical double bond and wherein $R_1$, $R_2$, $R_3$, $R_4$, $R_5$, $R_6$ and $R_7$ are defined as follows:

$R_1$ is selected from the group consisting of hydrogen, lower alkyl optionally interrupted by 1 to 3 ether linkages, $-R_{1b}-(CO)-R_{1a}$ and $-R_{1b}-(SO_2)-R_{1a}$ where $R_{1b}$ is NH, lower alkyl-substituted amino, S, O, $CH_2$ or CHOH, and $R_{1a}$ is lower alkyl optionally interrupted by 1 to 3 ether linkages, cycloalkyl, lower alkenyl, aryl of 1 to 2 rings, alkoxy, alkenyloxy, hydroxyalkoxy, dihydroxyalkoxy, aminoalkyl, N-protected aminoalkyl, or amino $NR_{1c}R_{1d}$ where $R_{1c}$ and $R_{1d}$ are independently selected from the group consisting of hydrogen and lower alkyl optionally interrupted by 1 to 3 ether linkages, or are linked together to form a piperidino or morpholino ring;

$R_2$ is selected from the group consisting of lower alkyl, cycloalkyl methylene, benzyl, halobenzyl, lower alkyl-substituted benzyl, lower alkoxy-substituted benzyl, amino-substituted naphthyl, lower halonaphthyl, lower alkyl-substituted naphthyl, lower alkoxy-substituted naphthyl, amino-substituted naphthyl, phenethyl, phenoxy, thiophenoxy, and anilino;

$R_3$ is hydrogen or lower alkyl;

$R_4$ is selected from the group consisting of lower alkyl, lower alkenyl, alkoxy-substituted lower alkyl, alkoxy-substituted lower alkenyl, benzyl, and heterocyclic ring substituted methylene;

$R_5$ is selected from the group consisting of lower alkyl, cycloalkyl methyl, (1,3-dithiolan-2-yl)methylene and benzyl;

$R_6$ is selected from the group consisting of hydrogen, lower alkyl, vinyl and arylalkyl; and $R_7$ is selected from the group consisting of hydrogen and lower alkyl, with the proviso that $R_6$ and $R_7$ are not both hydrogen.

Another novel class of compounds herein has the structural formula

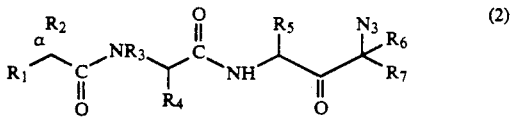

(2)

wherein "α" and the "R" substituents $R_1$ through $R_7$ are as defined above, although here $R_6$ and $R_7$ may, if desired, both be hydrogen. It may be seen that these hydroxyazido analogs are actually ketoazido compounds.

The invention also encompasses pharmaceutically acceptable esters and salts of such compounds.

In another aspect, the invention provides pharmaceutical compositions containing one or more of the novel compounds in combination with a pharmaceutically acceptable vehicle or carrier. In a preferred embodiment, the compositions are formulated for oral administration.

In still another aspect, the invention provides a method for treating hypertension, the method comprising administering to an individual in need of such treatment one or more of the aforementioned novel compounds within the context of a dosage regimen effective to treat hypertension as will be described in detail herein.

DETAILED DESCRIPTION OF THE INVENTION

In this specification and in the claims which follow reference will be made to a number of terms which shall be defined to have the following meanings:

"Alkyl" refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. "Lower alkyl" refers to an alkyl group of one to eight, more preferably one to six, carbon atoms, and thus includes, for example, methyl, ethyl, n-propyl, isopropyl, n-butyl, isobutyl, t-butyl and octyl.

"Alkenyl" refers to a branched or unbranched unsaturated hydrocarbon group of 2 to 24 carbon atoms and one or more unsaturated carbon-carbon bonds, such as for example, ethenyl, 1-propenyl, 2-propenyl, 1-butenyl, 2-isobutenyl, octenyl, decenyl, tetradecenyl, $\Delta^{8,11}$-heptadecadienyl, hexadecenyl, eicosenyl, tetracosenyl and the like. "Lower alkenyl" refers to an alkenyl group of two to eight, more preferably two to six, carbon atoms, and thus includes, for example, ethenyl, 1-propenyl, 2-propenyl, 1-butenyl, 2-isobutenyl and octenyl.

"Alkenyloxy" represents an alkenyl group as defined above appended to an oxy radical.

"Alkoxy" refers to an alkyl group as defined above appended to an oxy radical.

"Alkylene" refers to a difunctional saturated branched or unbranched hydrocarbon chain containing from 1 to 6 carbon atoms, and includes, for example, methylene ($-CH_2-$), ethylene ($-CH_2-CH_2-$), propylene ($-CH_2-CH_2-CH_2-$), 2-methylpropylene [$-CH_2-CH(CH_3)-CH_2-$], hexylene [$-(CH_2)_6-$] and the like.

The term "amino" as used herein refers to an $-NH_2$ substituent. The term "alkylamino" as used herein refers to an amino group substituted with a single alkyl group, wherein "alkyl" is as defined above. The term "aminoalkyl" refers to an "alkyl" group as defined above substituted with an amino moiety.

"Aryl" refers to a phenyl or 1- or 2-naphthyl group. Optionally, these groups are substituted with one to three, more preferably one to two, lower alkyl, lower alkoxy, hydroxy, amino, nitro and/or mercapto substituents.

"Arylalkylene" refers to an aryl group as is defined herein which is attached to one end of an alkylene group as is defined herein.

"Cycloalkyl" refers to a saturated hydrocarbon ring group having from 3 to 8 carbon atoms, and includes, for example, cyclopropyl, cyclobutyl, cyclopentyl, cycloheptyl, cyclohexyl, methylcyclohexyl, cyclooctyl, and the like.

"Cycloalkyl alkylene" refers to a saturated hydrocarbon containing a cycloalkyl group as is defined herein attached to one end of an alkylene group as is defined herein. The term includes, for example, cyclohexyl methylene, cyclopropyl methylene, cyclobutyl ethylene, 6-cyclooctyl hexylene, and the like.

"Halo" or "halogen" refers to fluoro, chloro, bromo or iodo, usually regarding halo substitution for a hydrogen atom in an organic compound. Of the halos, chloro and bromo are generally preferred with chloro generally being the more preferred.

"Haloalkyl" refers to an "alkyl" group in which one or more of its hydrogen atoms is substituted by a "halogen" group.

"Haloaryl" refers to an "aryl" group substituted with one or more halogen groups.

"Heterocyclic" as used herein refers to any 5- or 6-membered ring containing from one to three heteroatoms, or to any bicyclic compound containing such a 5- or 6-membered ring, wherein the heteroatoms are independently selected from the group consisting of nitrogen, oxygen and sulfur. Nitrogen atoms, if present, may be oxidized or quaternized, and sulfur atoms, if present, may be oxidized as well. If 5-membered, the ring may contain from 0 to 2 double bonds; if 6-membered, the ring may contain from 0 to 3 double bonds. Preferred heterocyclic moieties are aromatic, i.e., fully saturated and particularly preferred heterocyclic moieties are nitrogen-containing. Examples of preferred heterocyclic compounds are pyrryl, pyrrolinyl, pyrrolidinyl, pyrazolyl, pyrazolinyl, pyrazolidinyl, imidazolyl, imadazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl. Heterocyclic moieties may be unsubstituted, monosubstituted or disubstituted with hydroxy, oxo, amino, alkylamino, dialkylamino, alkoxy, lower alkyl, halogen or haloalkyl. The most preferred heterocyclics are as follows:

wherein k is 1 or 2 and X is N, NH, O or S, and the "*" represents the point of attachment;

wherein Y is NH, N-lower alkyl, O, S or $SO_2$; and (i)

(ii)

and (iii)

wherein the symbols (i), (ii) and (iii) represent 5-membered heterocycles containing one or more heteroatoms and containing 2 double bonds and wherein $Z_1$ and $Z_2$ are independently selected from the group consisting of N, O and S.

"N-protecting group" as used herein denotes a substituent bound to a nitrogen atom. Typically, the substituent is intended to protect the amino group against undesirable reactions during synthetic procedures (and, in the case of a protecting group which protects the N-terminus of an amino acid, the group is intended to prevent the attack of exopeptidases on the compounds). Examples of N-protecting groups for use herein are sulfonyl, acyl, acetyl, pivaolyl, t-butyloxycarbonyl ("Boc"), carbonylbenzyloxy ("Cbz"), and benzoyl.

"Optional" or "optionally" means that the subsequently described aspect of the invention may or may not be present, and that the description includes instances where said aspect occurs and instances in which it does not. For example, lower alkyl "optionally interrupted by either linkages" means that ether linkages may or may not be present, and that the description includes both lower alkyl groups containing ether linkages and lower alkyl groups which do not contain ether linkages. Similarly, the symbol "α" in Formula (1) represents an "optional double bond" in that $R_2$ may be connected to the adjacent carbon atom through either a single bond or a double bond, and the invention encompasses both of these options.

In chemical structures, the symbols "α" and "β" indicate the specific stereochemical configuration of a substituent at an asymmetric carbon atom in a chemical structure as drawn. Thus "α", denoted by a broken line, indicates that the group at the position in question is below the general plane of the molecule as drawn, and "β", denoted by a bold line, indicates that the group at the position in question is above the general plane of the molecule as drawn. The terms "R" and "S" also have their conventional meaning, i.e., as defined by the IUPAC 1974 Recommendations for Section E, Fundamental Stereochemistry, *Pure Appl. Chem.* 45:13-30 (1976).

The chiral centers of the compounds of the invention may have either the "R" or "S" configuration; however, certain configurations are preferred. For example, it is preferred that the hydroxyazido portion of the molecule be such that the 4-position (where the azido is present) is "S" and 5-position (where the hydroxy group is present) is "R." This is illustrated in the following structure:

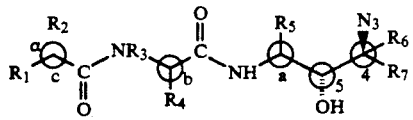

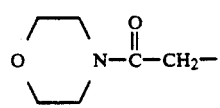

or wherein $R_1$ is

It is also preferred that the other, circled chiral centers designated "a" and "b" be in the "S" configuration, and that the chiral center designated "c" be in a configuration analogous to that of an L-amino acid.

The novel renin inhibiting compounds of the invention thus have the structure shown as Formulae (1) and (2) above, wherein the various substituents $R_1$, $R_2$, $R_3$, $R_4$, $R_5$, $R_6$ and $R_7$ are as just defined. Preferred compounds within the scope of Formulae (1) and (2) are wherein $R_1$ is selected from the group consisting of:

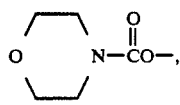

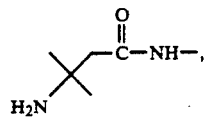

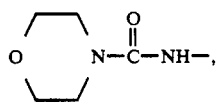

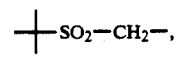

and

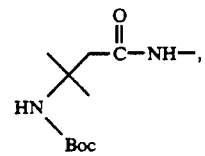

In the preferred embodiment, $R_2$ is preferably lower alkyl or benzyl, while $R_3$ is preferably hydrogen, and $R_4$ is preferably imidazolyl methyl (such that a histidine residue is present in the molecular structure of Formula 1). $R_5$ is preferably cycloalkyl methyl, e.g., cyclohexyl ethyl, while $R_6$ is preferably hydrogen and $R_7$ is preferably lower alkyl.

The following compounds exemplify particular compounds within the generic groups defined by Formulae (1) and (2):

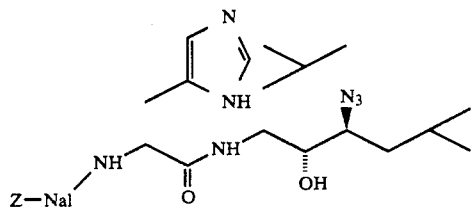

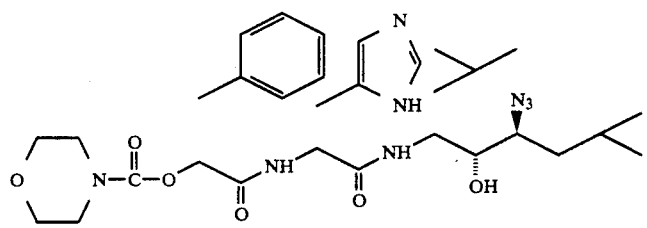

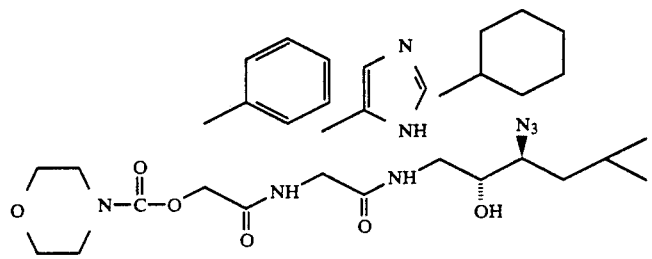

-continued
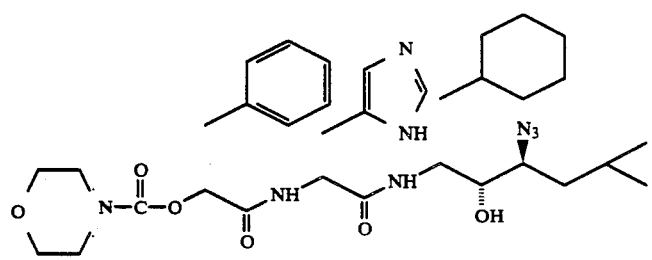
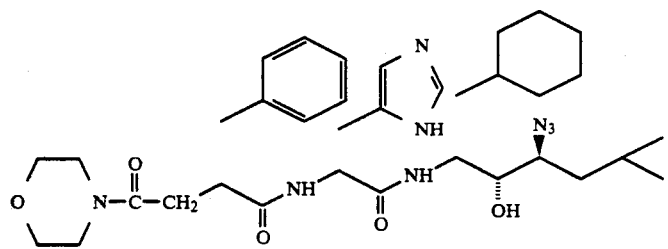
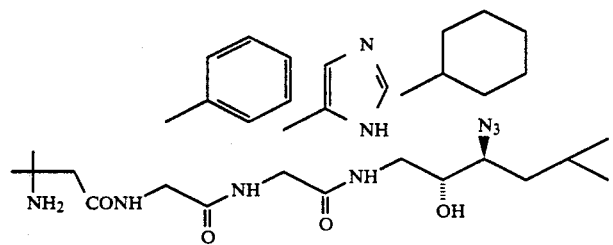
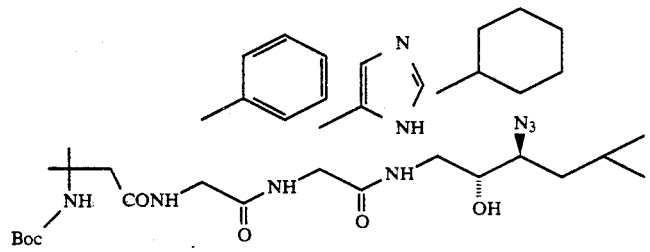
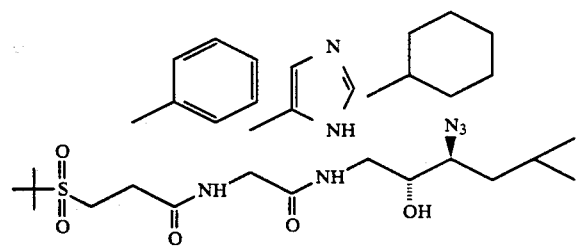
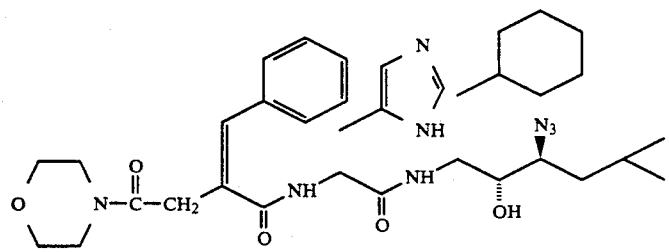

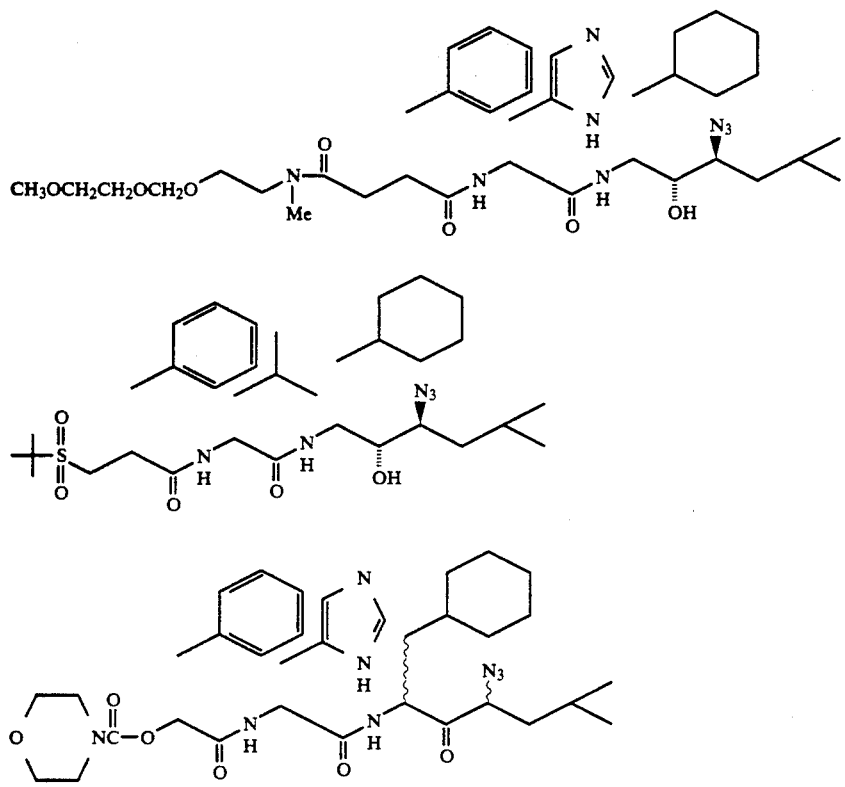

The compounds of the invention which contain a free amine group or an imidazole moiety can be used in the form of pharmaceutically acceptable acid addition salts, i.e., salts which retain the biological effectiveness and properties of the free bases and which are not biologically or otherwise undesirable, formed with inorganic acids such as hydrochloric acid, hydrobromic acid, sulfuric acid, nitric acid, phosphoric acid or the like, or from organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, or the like.

The invention also encompasses pharmaceutically acceptable basic salts in which one or more of the nitrogen-containing groups is quaternized with, for example, lower alkyl halides, such as methyl, ethyl, propyl or butyl chloride, bromide or iodide, with dialkyl sulfates such as dimethyl, diethyl, dibutyl or diamyl sulfate, with long chain halides such as decyl, lauryl, myristyl and stearyl chloride, bromide or iodide, or with aralkyl halides like benzyl and phenethyl bromides and others.

Conversion between these various salt forms may be carried out as follows. The compounds of Formulae (1) or (2) in free base form may be converted to the acid addition salts by treatment with a stoichiometric excess of the appropriate inorganic or organic acid. Typically, the compound in free base form is dissolved in a polar organic solvent such as ethanol or methanol, and the acid added thereto. The temperature is maintained in the range of about 0° C. to about 100° C. The resulting acid addition salt precipitates spontaneously or may be brought out of solution with a less polar solvent. Conversely, acid addition salts may be converted to the corresponding free base by treatment with a stoichiometric excess of a suitable base, such as potassium carbonate or sodium hydroxide, typically in the presence of aqueous solvent, and at a temperature in the range of about 0° C. to about 100° C. The free base form may be isolated by conventional means, such as extraction with an organic solvent. Various salts may be interchanged by taking advantage of differential solubilities of the salts, or differential volatilities or acidities of the acids, or by treatment with an appropriately loaded ion exchange resin. For example, interchange of two acid addition salts may be effected by reaction of one salt with a slight stoichiometric excess of an acid of a lower $pK_a$ than the acid component of the starting salt. This conversion will typically be carried out at a temperature between about 0° C. and the boiling point of the solvent used as the medium for the procedure.

The components of the invention can also be used in the form of esters. Examples of preferred esters include a hydroxyl-substituted compound of the invention which has been acylated with a blocked or unblocked amino acid residue, a phosphate function, or a hemisuccinate residue. The amino esters of particular interest are glycine and lysine; however, other amino acid residues can also be used. These esters serve as prodrugs of the compounds of the invention and are intended to increase solubility in the gastrointestinal tract. The preparation of these prodrug esters is carried out by reacting a hydroxyl-substituted compound of the invention with an activated amino acyl, phosphoryl or hemisuccinyl derivative. The resulting product is then deprotected to provide the desired prodrug ester.

Methods of preparing the novel compounds are exemplified in detail in the Examples herein. Generally, synthetic methods for obtaining the novel compounds are analogous to those described in a number of the patents cited in the above section entitled "Pertinent Art", in particular in U.S. Pat. Nos. 4,927,807 to Stein et al., 4,645,759 to Luly et al., 4,826,815 to Luly et al., and 4,857,507 to Rosenberg et al., the disclosures of which are incorporated by reference in their entirety.

A preferred method of synthesizing the hydroxyazido compounds of the invention involves initial preparation of the fragment

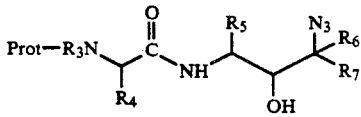 (3)

where "Prot" is an amino protecting group and the substituents $R_3$ through $R_7$ are as defined above. Preparation of this material typically involves reaction of an alkenyl-containing compound through an epoxide intermediate. Fragment (3) is then reacted with the carboxylic acid

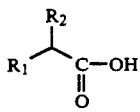 (4)

to form the amide product. Ketoazido analogs are made in a similar manner; the final hydroxyazido product is simply oxidized to the ketoazido compound with a suitable oxidizing agent.

The compounds disclosed and claimed herein are useful as renin inhibitors to treat hypertension. In addition to their utility in treating hypertension, the renin inhibitors of the invention are also potentially useful to treat congestive heart failure or glaucoma, or may be useful as HIV protease inhibitors.

In the preferred embodiment, the present compounds are used within the context of a dosing regimen effective to treat hypertension. The compounds may be used along, or in combination with one or more other types of drugs, e.g., diuretics. A number of suitable dosing regimens have been developed for the administration of renin inhibitors to treat hypertension, and are well-known in the art. Total daily dose administered to an individual in single or divided doses may be, for example, from about 0.001 to 10 mg/kg body weight and more usually 0.01 to 1 mg. The specific dose level for any particular patient, however, will of course be dependent on the subject being treated, i.e., on the subject's age, body weight, general health, sex, diet, time of administration, route of administration, rate of excretion, severity of the particular disease undergoing therapy, and the like, as well as on the activity of the particular compound administered.

Administration of the active compounds described herein can be via any of the accepted modes of administration of therapeutic agents. These methods include oral, parenteral, intravenous, transdermal, subcutaneous, pulmonary, intranasal, rectal and other systemic modes. For those compounds herein which are orally active, oral administration is the preferred mode. For those compounds which are not orally active, administration in the form of a long-acting injectable composition is preferred.

Depending on the intended mode of administration, the compositions may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will preferably include a conventional pharmaceutical vehicle or excipient and one or more of the present renin inhibitors or esters or salts thereof and, in addition, may include other medicinal agents, pharmaceutical agents, carriers, adjuvants, diluents, etc.

For solid compositions, conventional nontoxic solids include, for example, pharmaceutical grades of mannitol, lactose, starch, magnesium stearate, sodium saccharin, talc, cellulose, glucose, sucrose, magnesium carbonate, and the like may be used. The active compound as defined above may be formulated as suppositories using, for example, a polyalkylene glycol, as the carrier.

Liquid pharmaceutically administrable compositions can, for example, be prepared by dissolving, dispersing, etc. an active compound as defined above and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc.

Actual method of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, for purposes of treating hypertension, contain an effective amount of the desired renin inhibitor, i.e., an amount effective to achieve the desired therapeutic effect in the subject being treated.

For oral administration, i.e., of any of the present compounds which may be orally active, a pharmaceutically acceptable nontoxic composition is prepared by the incorporation of any of the normally employed excipients described above. Such compositions take the form of solutions, suspensions, tablets, pills, capsules, powders, sustained-release formulations and the like. Such compositions may contain 1%-95% active ingredient, preferably 1-10%.

Parenteral administration, if used, is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of nontoxic auxiliary substances such as wetting or emulsifying agents, pH buffering agents and the like, such as, for example, sodium acetate, sorbitan monolaurate, triethanolamine oleate, etc. A more recently revised approach for parenteral administration employs the implantation of a slow-release or sustained-release system, such that a constant level of dosage is maintained.

The following examples are intended to provide those of ordinary skill in the art with a complete disclosure and description of how to make the novel compounds of the invention, and are not intended to limit the scope of what the inventor regards as his invention in any way. Efforts have been made to insure accuracy with respect to numbers used (e.g., amounts, temperatures, etc.), but some experimental error and deviation should, of course, be allowed for. Unless indicated otherwise, parts are parts by weight, temperatures are in degrees centigrade, and pressure is at or near atmospheric.

EXAMPLE 1

This example describes preparation of 4-azido-6-(S)-[N$^\alpha$-[N-benzyloxycarbonyl-3-(1-naphthyl)-L -alanyl]-L-histidyl]-amino-2,8-dimethyl-5-nonanol as illustrated in Scheme I.

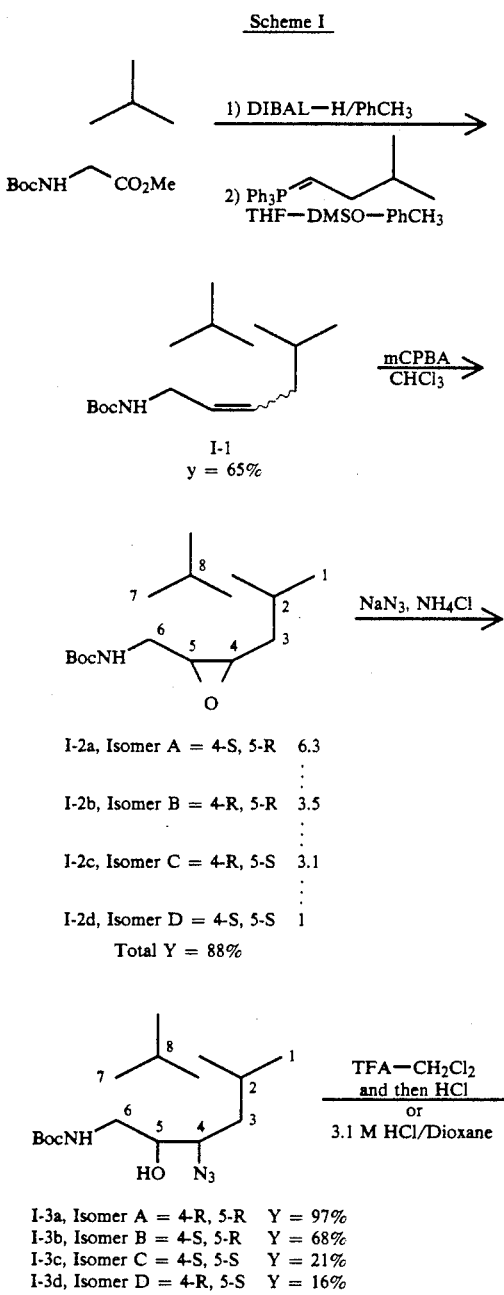

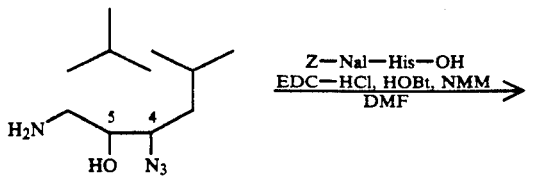

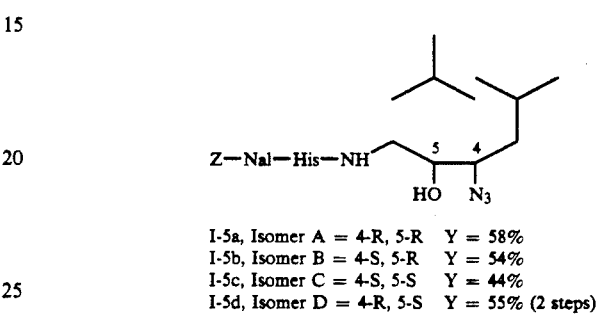

I-5a, Isomer A = 4-R, 5-R   Y = 58%
I-5b, Isomer B = 4-S, 5-R   Y = 54%
I-5c, Isomer C = 4-S, 5-S   Y = 44%
I-5d, Isomer D = 4-R, 5-S   Y = 55% (2 steps)

a. 6-(S)-(t-Butyloxycarbonyl)amino-2,8-dimethyl-4-nonene (I-1). To a stirred −78° C. solution of 3.72 g (15.2 mmol) of Boc-Leu-OMe in 40 mL of dry toluene was added 19.7 mL of a 1.0M solution of diisobutylaluminum hydride in hexane at a rate to keep the internal temperature below −60° C. After sintering for an additional 20 min at −78° C., the aldehyde solution was used immediately as described below.

To a stirred 0° C. solution of 13.8 g (33.4 mmol) of triphenylisopentyl phosphonium bromide in 136 mL of 5:1 tetrahydrofuran/dimethyl sulfoxide was added dropwise 66.7 mL of a 0.5M solution of potassium bis(-trimethylsilyl)amide in toluene. The mixture was stirred vigorously for 1 h, at which time it was cooled to −78° C.

To the cooled Wettig reagent solution was added via canula the −78° C. aldehyde solution prepared above. After being stirred to −78° C. for 20 min, the reaction mixture was allowed to slowly warm to room temperature, and then heated to 40° C. for 12 h. The mixture was then cooled to room temperature and quenched with 830 μL of methanol followed by 72 mL of aqueous Rochelle salts (12 mL of saturated solution a60 mL of water). The mixture was then extracted with ethyl acetate (3×60 ml). The combined extracts were washed with water and saturated brine, dried over MgSO$_4$, filtered, and evaporated under reduced pressure. Purification of the residue by flash chromatography using 25:1 hexane/ethyl acetate provided 2.64 g (Y - 64.6%) of I−1 as a colorless oil; NMR (90 MHz, CDCl$_3$) δ0.75∼1.05 (m, 12H), 1.05∼2.2 (m, 6H), 3.8∼4.6 (m, 2H), 5.0∼5.75 (m, 2H); MS m/e (M+H+) 270, (M-C$_4$H$_8$)+H+) 214.

b. 6-(S)-(t-Butyloxycarbonyl)amino-2,8-dimethyl-4,5-epoxynonane (I-2). A solution of 3.12 g (11.6 mmol) of nonene derivative I−1 in 180 mL of dichloromethane was treated with 3-chloroperoxybenzoic acid and allowed to stand at room temperature for 19 h. To the concentrated reaction mixture was added 200 mL of ethyl acetate and 90 mL of cold 10% aqueous Na$_2$S$_2$O$_3$, and this mixture was stirred vigorously at 0°∼5° C. for 1.5 h. The organic phase was washed with saturated aqueous NaHCO$_3$ and saturated brine, dried over MgSO$_4$, filtered, and evaporated under reduced pressure. Separation by flash chromatography using 50:1~20:1 hexane/ethyl acetate gave 1.32 g of isomer A (I-2a) as a white solid, 741 mg of isomer B (I-2b) as a colorless oil, 645 mg of isomer C (I-2c) as a white solid, 211 mg of isomer D (I-2d) as a white solid in 80% total yield of four isomers. The analytical data for the four isomers is as follows:

I-2a (5-R, 4-S epoxide): R$_f$ 0.23 (9:1 hexane/ethyl acetate); NMR (90 MHz, CDCl$_3$) δ0.8~1.1 (m, 12H), 1.46 (s, 9H), 1.1, 2.1 (m, 6H), 2.80 (dd, 4.2, 7.2 Hz, 1H), 3.02 (dt, J=4.2, 7.2 Hz, 1H), 3.3~3.8 (m, 1H), 4.52 (brd, J=9.1, 1H); MS m/e (M+H$^+$) 286, (m-C$_4$H$_8$)+H$^+$) 230.

I-2b (5-R, 4-R epoxide): R$_f$ 0.45 (9:1 hexane/ethyl acetate); NMR (90 MHz, CDCl$_3$) δ0.96 (d, J=6.3 12H), 1.45 (s, 9H), 1.1~2.1 (m, 6H), 2.70 (d, J=2.0 Hz, 1H), 2.80 (dt, J=2.0 5.5 Hz, 1H), 3.7~4.1 (m, 1H), 4.33 (brd, J=9.3 Hz, 1H); MS m/e (M+H$^+$) 286, (M-C$_4$H$_8$)+H$^+$) 230.

I-2c (5-S, 4-R epoxide): R$_f$ 0.32 (9:1 hexane/ethyl acetate); NMR (90 MHz, CDCl$_3$) δ0.8~1.1 (m, 12H), 1.46 (s, 9H) 1.1~2.1 (m, 6H) 2.69 (d, J=3.6, 7.2 Hz, 1H), 2.00 (dt, J=3.5, 7.2 Hz, 1H) 4.2~4.6 (brd, J=9.1 Hz, 1H); MS m/e (M+H$^+$) 286, (M-C$_4$H$_8$)+H$^+$) 230.

I-2d (5-S, 4-S epoxide): R$_f$ 0.40 (9:1 hexane/ethyl acetate; NMR (90 MHz, CDCl$_3$) δ0.8~1.1 (m, 12H), 1.47 (s, 9H), 1.1~2.1 (m, 6H), 2.55 (d, J=2.0, 6.4 Hz, 1H), 3.00 (dt, J=2.0, 5.4 Hz, 1H), 3.2~3.7 (m, 1H), 4.2~4.5 (brd, J=8.2 Hz, 1H); MS m/e (M+H$^+$) 286, ((M-C$_4$H$_8$)+H$^+$) 230.

General Procedure for Epoxide Opening Reaction of 4-(t-Butyl-oxycarbonyl)amino-2,8-dimethyl-5,6-epoxide (I-2) with Azide.

Isomer A of 6-(S)-(t-butyloxycarbonyl)amino-4-azido-2,8-dimethyl-5-nonanol (I-3a). A solution of 428 mg (1.5 mmol) of I-2a, 975 mg (15.0 mmol) of sodium axide and 602 mg (11.2 mmol) of ammonium chloride in 30 mL of methanol was heated to reflux for 43 h. The reaction mixture was partitioned between chloroform and water. The aqueous layer was washed with two portions of chloroform. The combined organic phase was dried over MgSO$_4$, filtered, and evaporated under reduced pressure. Purification of the residue by flash chromatography using 15:1 hexane/ethyl acetate gave 477 mg (Y=97%) of I-3A (5R, 6-R isomer) as a colorless glassy solid; NMR (90 MHz, CDCl$_3$) δ0.8~1.0 (m, 12H), 1.44 (s, 9H), 1.1~2.1 (m, 6H), 3.08 (brs, 1H), 3.2~3.5 (m, 2H), 3.6~4.0 (m, 1H), 4.84 (brd, J=9.7 Hz, 1H); MS m/e (M=H$^+$) 329, ((M-C$_4$H$_8$)+H$^+$) 273, ((M-C$_5$H$_8$O$_2$)+H$^+$) 229; Anal. Calcd. for C$_{16}$H$_{32}$N$_4$O$_3$: C, 58.51; H, 9.82; N, 17.06. Found: C 58.67; H, 9.90; N, 17.00.

Isomer B, I-3b (5-R, 4-s isomer): Y=68%; NMR (90 MHz, CDCl$_3$)δ0.8~1.1 (m, 12H), 1.45 (s, 9H), 1.1~2.1 (m, 6H), 3.1~3.5 (m, 3H), 3.5~3.9 (m, 1H) 4.73 (brd, J=8.3 Hz, 1H); MS m/e (M+H$^+$) 329, (M-C$_4$H$_8$)+H$^+$) 273, ((M-C$_5$H$_8$O$_2$)+H$^+$) 229; Anal. Calcd. for C$_{16}$H$_{32}$N$_4$O$_3$: C, 58.51; H, 9.82; N, 17.06. Found: C, 58.36; H, 9.82; N, 17.08.

Isomer C, I-3c (5-S, 4-S isomer): Y=21%, NMR (90 MHz, CDCl$_3$)δ0.8~1.1 (m, 12H), 1.45 (s, 9H), 1.1~2.1 (m, 6H), 2.72 (brd, J=5.4, 1H), 3.1~3.6 (m, 2H), 3.6~4.0 (m, 1H), 4.67 (brd, J=9.0 Hz, 1H); MS m/e (M+H$^+$) 329, (M-C$_4$H$_8$)+H$^+$) 273, ((M-C$_5$H$_8$O$_2$)+H$^+$) 229; Anal. Calcd. for C$_{16}$H$_{32}$N$_4$O$_3$1/8 hexane: C, 59.31; H, 10.03; N, 16.52. Found: C, 59.32; H, 9.88; N, 16.28.

Isomer D, I-3d (5-S, 4-R isomer): Y=16%, NMR (90 MHz, CDCl$_3$) δ0.8~1.1 (m, 12H), 1.44 (s, 9H), 3.0~4.0 (m, 3H) 4.56 (brd, J=9.0 Hz, 1H); MS m/e (M+H$^+$) 329, ((M-C$_4$H$_8$)+H$^+$) 273, ((M-C$_5$H$_8$O$_2$)+H$^+$) 229; Anal. Calcd. for C$_{16}$H$_{32}$N$_4$O$_3$1/8 hexane: C, 59.31; H, 10.03; N, 10.52. Found: C, 58.99; H, 9.92; N, 10.19.

General Procedure for Deprotection of 6-(S)-(t-Butyloxy-carbonyl)amino-4-azido-2,8-dimethyl-5-nonanol (I-3).

Isomer A of 6-(S)-Amino-4-azido-2,8-dimethyl-5-nonanol (I-4a). A solution of 225 mg (0.685 mmol of I-3a in 4 mL of 1:1 trifluoroacetic acid/dichloromethane was stirred at room temperature for 1 h. After concentration, the residue was partitioned between dichloromethane and saturated aqueous NaHCO$_3$. The aqueous layer was washed with two portions of dichloromethane. The combined organic phases were dried over MgSO$_4$, filtered, and evaporated. To the residue was added 3 mL of a 3.1M solution of HCl in dioxane. After being dissolved and evaporated, the residue was triturated with ethyl ether to give 141 mg (Y=78%) of I-4a hydrochloride as a white solid. This material was used without further purification.

Isomer B (I-4b). A solution of 230 mg (0.700 mmol) of I-3b in 5 mL of a 3.1M solution of HCl in dioxane was stirred at room temperature for 2 h. After concentration, triturating the residue with ethyl ether provided 115 mg (Y=62%) of I-4b hydrochloride as a white solid. This material was used without further purification.

Isomer C (I-4c). I-4c was obtained from I-3c in 62% yield according to the procedure for preparation of I-4a hydrochloride. This material was used without further purification.

Isomer D (I-4d). Following the procedure for preparation of I-4b, a quantitative yield of crude I-4d was obtained.

General Procedure for Coupling 6-Azido-4-(S)-amino-2,8-dimethyl-5-nonanol (I-4) to Z-Nal-His.

Isomer A of 4-Azido-6-(S)-[N$^\alpha$-[N-benzyloxycarbonyl-3-(1-naphthyl)-L-alanyl]-L-histidyl]-amino -2,8-dimethyl-5-nonanol I-5A). A solution of 79.4 mg (0.300 mmol) of I-4a hydrochloride, 160.5 mg (0.330 mmol) of Z-Nal-His-OH, 121.6 mg (0.900 mmol) of 1-hydroxybenzotriazole monohydrate, and 99 μl (0.900 mmol) of N-methyl-morpholine in 5.3 mL of N,N-dimethylformamide was cooled to −20° to −30° C. and treated with 64.5 mg (0.330 mmol) of 1-ethyl-3-[3-(dimethylamino)propyl]-carbodiimide hydrochloride. The resulting solution was stirred at −20° to −30° C. for 2 h, and slowly allowed to warm to ambient temperature overnight. The resulting solution was partitioned between ethyl acetate and saturated aqueous NaHCO$_3$. The organic phase was washed with saturated brine, dried over MgSO$_4$, filtered, and evaporated under reduced pressure. Purification of the residue by flash chromatography using 3% saturated methanolic ammonia/dichloromethane provided 122 mg (Y=58%) of I-5a; NMR (400 MHz, CDCl$_3$) δ0.81 (d, J=6.0 Hz, 6H), 0.96 (d, J=6.6 Hz, 3H), 0.98 (d, J=6.4 Hz), 1.04~1.23 (m, 2H), 1.30~1.42 (m, 1H), 1.43~1.55 (m, 2H) 1.76~1.90 (m, 1H), 2.88 (d, J=4.8, 14.5 Hz, 1H), 3.22

(d, J=2.4, 14.5 Hz, 1H), 3.26~3.42 (m, 2H), 3.80~3.89 (m, 1H), 4.03~4.13 (m, 1H), 4.48~4.56 (m, 1H), 4.56~4.63 (m, 1H), 4.98 (d, J=14.0 Hz, 1H), 5.02 (d, J=14.0 Hz, 1H), 5.31 (s, 1H), 5.39 (brs, 1H), 6.60 (d, J=10.0 Hz, 1H), 6.79 (s, 1H), 7.21 (s, 1H), 7.25~7.43 (m, 8H), 7.50~7.61 (m, 2H), 7.81 (d, J=7.1 Hz, 1H), 7.89 (d, J=7.1 Hz, 1H), 8.19 (d, J=7.2 Hz, 1H), 8.50 (brs, 1H); MS m/e (M+H+) 697, (M-C$_7$H$_8$O)+H+) 589, (M-C$_5$H$_{11}$N$_3$)+ H+) 584 (M-C$_{12}$H$_{17}$N$_3$O) 476; Anal. Calcd. for C$_{38}$H$_{48}$N$_8$O$_5$·½H$_2$O: C, 64.66; H, 7.00; N, 15.87. Found C, 64.64; H, 6.85; N, 15.22.

Isomer B (I-5b): NMR (400 MHz, CDCl$_3$) δ0.84 (d, J=5.7 Hz, 3H), 0.86 (d, J=5.4 Hz, 3H), 0.98 (d, J=6.6 Hz, 6H), 1.12~1.30 (m, 2H), 1.34~1.45 (m, 1H), 1.48~1.67 (m, 2H), 1.80~1.92 (m, 1H), 2.89 (d, J=5.3, 15.0 Hz, 1H), 3.18~3.36 (m, 3H), 3.87 (d, J=4.1, 13.9 Hz, 1H), 4.10~4.18 (m, 1H) 4.42~4.50 (m, 1H), 4.56~4.63 (m, 1H), 4.97 (d, J=12.4, 1H), 5.01 (d, J=1.24, 1H), 5.42 (brd, J=3.9 Hz, 1H), 6.63 (brd, J=9.1 Hz, 1H), 6.81 (s, 1H), 7.22, (s, 1H), 7.23~7.45 (m, 8H), 7.51~7.62 (m, 2H), 7.81 (d, J=7.9 Hz, 1H), 7.88 (d, J=7.7 Hz, 1H), 8.18 (d, J=8.6 Hz, 1H), 8.68 (brs, 1H); MS m/e (M+H+) 697, (M-C$_7$H$_8$O)+H+) 589, (M-C$_5$H$_{11}$N$_3$)+H+) 584 (M-C$_{12}$H$_{17}$N$_3$O)+H+) 476; Anal. Calcd. for C$_{38}$H$_{48}$N$_8$O$_5$: C, 65.50; H, 6.94; N, 16.08. Found: C, 65.64; H, 6.94; N, 15.99.

Isomer C (I-5c): NMR (400 MHz, CDCl$_3$) δ0.83 (d, J=6.0 Hz, 3H), 0.87 (d, J=6.2 Hz, 3H), 0.96 (d, J =6.7 Hz, 3H), 0.97 (d, J=6.6 Hz, 3H), 1.10~1.36 (m, 3H), 1.42~1.62 (m, 2H), 1.74~1.88 (m, 1H), 3.03 (d, J=4.4, 14.8 Hz, 1H), 3.13 (d, J=3.4, 14.8 Hz, 1H), 3.36~3.45 (m, 1H), 3.59 (t, J=4.5 Hz, 1H), 3.75 (d, J 5.4, 14.2 Hz, 1H), 3.97~4.08 (m, 1H), 4.48~4.60 (m, 2H), 4.99 (d, J=12.9 Hz, 1H), 5.02 (d, J=12.9 Hz, 1H), 5.43 (d, J=5.0 Hz, 1H), 6.51 (d, J=8.8 Hz, 1H), 6.70 (s, 1H), 7.26~7.42 (m, 9H), 7.46~7.58 (m, 2H), 7.77 (d, J =7.8 Hz, 1H), 7.86 (d, J=7.4 Hz, 1H), 7.84~7.94 (brs, 1H), 8.14 (d, J=8.1 Hz, 1H); MS m/e (M+H+) 697; Anal. Calcd. for C$_{38}$H$_{48}$N$_8$O$_5$: C, 65.50; H, 6.94; N, 16.08. Found: C, 65.03; H, 6.82; N, 15.80.

Isomer D (I-5d): NMR (400 MHz, CDCl$_3$) δ0.81 (d, J=6.2 Hz, 3H), 0.85 (d, J=6.4 Hz, 3H), 0.98 (d, J =6.4 Hz, 3H), 0.99 (d, J=6.6 Hz, 3H), 1.20~1.33 (m, 2H), 1.42~1.61 (m, 2H), 1.62~1.73 (m, 1H), 1.80~1.92 (m, 1H), 2.96 (d, J=5.0, 14.9 Hz, 1H), 3.17 (d, J=3.5, 14.9 Hz, 1H), 3.30~3.40 (m, 2H), 3.59 (dd, J=3.5, 7.9 Hz, 1H), 3.78~3.86 (m, 1H), 4.01~5.01 (m, 1H), 4.45~4.56 (m, 2H), 5.00 (s, 2H), 5.35 (d, J=4.3 Hz, 1H), 6.48 (d, J=8.6 Hz, 1H), 6.77 (s, 1H), 7.21~7.44 (m, 9H), 7.48~7.61 (m, 2H), 7.80 (d, J=7.9, 1H), 7.87 (d, J=7.1 Hz, 1H), 8.15 (d, J=8.2 Hz, 1H), 8.26 (brs, 1H); MS m/e (M+H+) 697; Anal. Calcd. for C$_{38}$H$_{48}$N$_8$O$_5$: C, 65.50; H, 6.94; N, 16.08. Found: C, 65.50; H, 6.91; N, 15.38.

EXAMPLE 2

This example describes the preparation of (2S)-2-(morpholino-N-carbonyloxy-)3-phenylpropionic acid as illustrated in Scheme II.

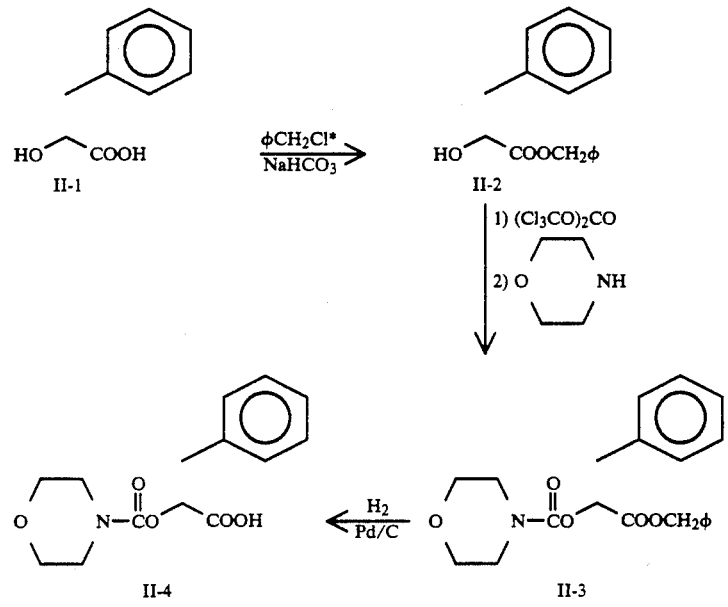

*φ = phenyl a. Benzyl (2S)-2-Hydroxy-3-phenylpropionate (II-2). To a suspended solution of L-3-phenyl-lactic acid (4.86 g, 29.3 mmol; obtained from Aldrich and designated compound II-1 in Scheme II), NaHCO$_3$ (5 g, 59.5 mmol) and a catalytic amount of NaI in DMF (15 mL) was added benzylchloride (4.45 g, 35.2 mmol), with stirring at room temperature. The stirring was continued at room temperature for 20 h and at 50° C. for 4 h. the reaction mixture was mixed with 1N HCl and extracted with AcOEt. The extract was washed with saturated NaHCO$_3$, H$_2$O and saturated NaCl, then dried (MgSO$_4$) and concentrated. The residue was purified by flash column chromatography on silica gel using AcOEt-n-hexane (1:3) as an eluant to give a colorless oil, II-2 (6.76 g, 90.9%). $^1$H-NMR (90 MHz, CDCl$_3$) δ2.24 (1H, d, J=8 Hz), 3.06 (2H, t, J=7 Hz), 4.50 (1H, td, J=8 Hz, 7 Hz), 5.19 (2H, s), 7.05-7.40 (10H, m).

b. Benzyl (2S)-2-(morpholino-N-carbonyloxy)-3-phenylpropionate (II-3). To a stirred solution of triphosgene (2.25 g, 7.60 mmol) in CH$_2$Cl$_2$ (5 mL) was added dropwise a solution of II-2 (4.75 g, 18.3 mmol) and pyridine (1.8 mL, 22.0 mmol) in CH$_2$Cl$_2$ (15 mL) for 15 min in ice-water batch. After stirring at the same temperature for 2 min, a solution of morpholine (4.8 mL, 54.9 mmol) in CH$_2$Cl$_2$ (15 mL) was added dropwise for 10 min. The stirring was continued for 30 min in ice-water bath. The solution was diluted with AcOEt and washed with H$_2$O, saturated NaHCO$_3$, 0.1N HCl, and saturated NaCl, then dried (MgSO$_4$) and concentrated. The residue was purified by flash column chromatography on silica gel using AcOEt/n-hexane (1:3) as an eluant to give a colorless oil, II-3 (6.36 g, 94.0%). TLC R$_f$ 0.53 (AcOEt-n-hexane, 1:2); $^1$H-NMR (90 MHz, CDCl$_3$) δ3.05–3.20 (2H, m), 3.20–3.64 (8H, m), 5.13 (1H, S), 5.16 (1H, s), 5.21 (1H, dd, J=9 Hz, 6 Hz), 7.05–7.35 (10H, m); MS m/e (M+) (369).

c. (2S)-2-(Morpholino-N-carbonyloxy-)-3-phenylpropionic Acid (II-4). A solution of II-3 (0.429 g, 1.16 mmol) in MeOH (15 mL) was treated with 10% Pd/C (0.049 g) and stirred under 1 atmosphere of H$_2$ for 2 h. The mixture was filtered and the filtrate was concentrated to dryness to give a colorless oil, II-4 (0.300 g, 92.6%). TLC R$_f$ 0.43 (CHCl$_3$-MeOH-AcOH, 90:10:1); $^1$H-NMR (CDCl$_3$, 90 MHz) δ3.00–3.27 (2H, m), 3.28–3.70 (8H, m) 5.19 (1H, dd, J=10 Hz, 8 Hz), 6.78 (1H, brs) 7.30 (5H, s); MS m/e (M+H+) 280.

EXAMPLE 3

This example described the preparation of (4S, 5R, 6S)-4-azido-5-hydroxy-2,8-dimethyl-6[N$^\alpha$-(2S-(morpholino-N-carbonyloxy)-3-phenylpropionyl)-L-histidyl]aminononane as illustrated in Scheme III.

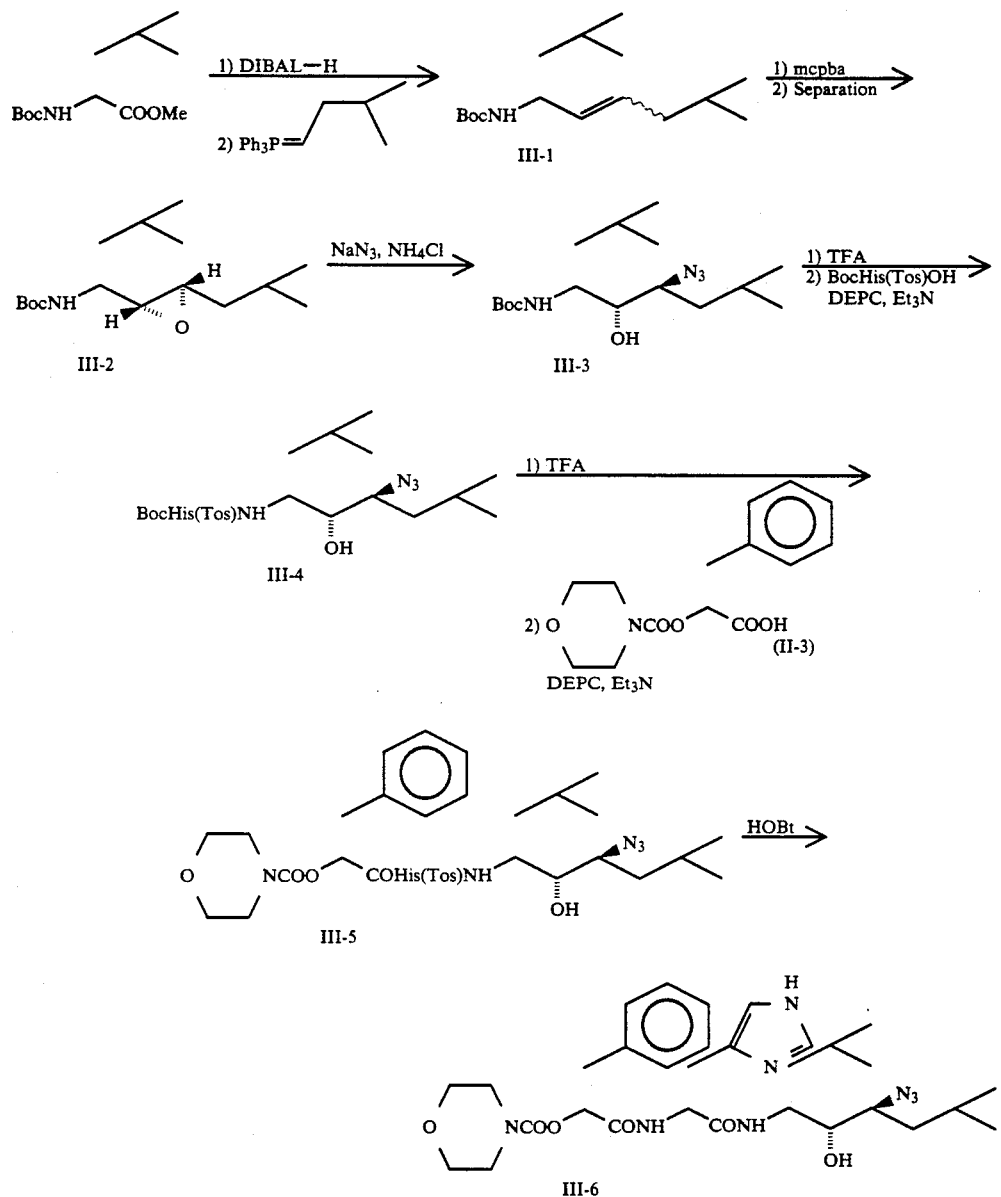

a. (6S-6-tert-Butoxycarbonylamino-2,8-dimethylnon-4-ene (III-1). To a stirred −78° C. solution of N-tert-butoxycarbonyl-L-leucine methylester (18.8 g, 76.8 mmol) in toulene (150 mL) was added diisobutyl aluminum hydride (1.5M solution in toluene, 71.1 mL, 106.7 mmol). After stirring for an addition 20 min at −78° C., the aldehyde solution was used immediately as described below.

To a stirred 0° C. suspension of isopentyltriphenylphosphonium bromide (63.8 g, 150 mmol) in toluene (200 mL) was added potassium bis(trimethylsilyl) amide (0.54M solution in toluene, 300 mL, 162 mmol). The mixture was stirred for 1 h at room temperature, then cooled to −78° C. The −78° C. aldehyde solution prepared above was added via cannula. After stirring at −78° C. for 20 min, the mixture was allowed to slowly warm to room temperature and was then quenched with methanol (6 mL) followed by saturated aqueous Rochelle salts (70 mL) and $H_2O$ (350 mL). The mixture was extracted with n-hexane. The extract was washed with $H_2O$ and saturated NaCl, then dried ($MgSO_4$) and concentrated. The residue was purified by flash chromatography using n-hexane-EtOAc (20:1) as an eluant to give a colorless oil, III-1 (8.87 g, 42.9%). TLC $R_f$ 0.39 (AcOEt-n-hexane, 1:20); $^1$H-NMR (90 MHz, $CDCl_3$) δ 0.91 (12H, d, J=7 Hz), 1.00–1.50 (4H, m), 1.45 (9H, s), 1.50–2.15 (2H, m), 4.00–4.51 (2H, m), 5.05–5.75 (2H, m).

b. (4R, 5R, 6S)-6-tert-Butoxycarbonylamino-4,5-epoxy-2,8-dimethylnonane (III-2). To a stirred solution of III-1 (11.7 g, 43.0 mmol) in $CH_2Cl_2$ (200 mL) was added a solution of m-chloroperbenzoic acid (80≧85%, 14.0 g, 64.9–69.0 mmol) in $CH_2Cl_2$ (300 mL) at room temperature. The stirring was continued for 10 h at room temperature and the solution was concentrated. The residue was dissolved in AcOEt and washed with 10% $Na_2S_2O_3$ (100 mL), saturated $NaHCO_3$, $H_2O$, and saturated NaCl, then dried ($MgSO_4$) and concentrated. The residue was purified by flash chromatography using n-hexane-AcOET (20:1) as an eluant to give a colorless oil, III-2 (3.28 g, 26.7%) and the other mixed isomers (5.96 g, 48.6%). TLC $R_f$ 0.61 (AcOET-n-hexane, 1:5); $^1$H-NMR (90 MHz, $CDCl_3$) δ 0.94 (3H, d, J=7 Hz), 0.95 (3H, d, J=7 Hz), 1.05–1.50 (4H, m), 1.42 (9H, s), 1.50–1.91 (2H, m), 2.70 (1H, dd, J=2 Hz, 0.5 Hz), 2.80 (1H, td, J=2 Hz, 5.5 Hz), 3.92 (1H, m), 4.40 (1H, brd, J=9 Hz).

c. (4S, 5R, 6S)-4-Azido-6-tert-butoxycarbonylamino-5hydroxy-2,8-dimethyl-nonane (III-3). A mixed suspension of III-2 (4.50 g, 16.0 mmol), $NaN_3$ 10.4 g, 160 mmol), and $NH_4Cl$ (6.4 g, 120 mmol) in MeOH (200 mL) was heated under reflex with stirring for 30 h. After concentration, the residue was partitioned between AcOEt and water. The organic layer was washed with $H_2O$ and saturated NaCl, then dried ($MgSO_4$) and concentrated. The residue was purified by flash chromatography using n-hexane-AcOEt (15:1) as an eluant to give a white solid III-3 (3.15 g, 59.9%). TLC $R_f$ 0.44 (AcOET-n-hexane, 1:4); $^1$H-NMR (90 MHz, $CDCl_3$) δ 0.92 (6H, d, J=7 Hz), 0.95 (6H, d, J=7 Hz), 1.48 (9H, s), 1.10–2.05 (6H, m), 3.30 (3H, brs), 3.75 (1H, m), 4.73 (1H, brd, J=8 Hz); MS m/e (M+H+) 329, (M—$C_5H_{10}N_3O$) 216, (M—$C_6H_{12}N_3O$) 186. Anal. Calcd. for $C_{16}H_{32}H_4O_3$: C, 58.51; H, 9.82; N, 17.06. Found: C, 58.60; H, 9.89; N, 17.10.

d. (4S, 5R, 6S)-4-Azido-6-($N^α$-tertbutoxycarbonyl-$N^{im}$-tosyl-L-histidyl)amino-5-hydroxy-2,8-dimthylnonane (III-4). Compound III-3 (0.297 g, 0.90 mmol) was dissolved in trifluoroacetic acid ("TFA," 1 mL) and $CH_2Cl_2$ (2 mL), and stirred for 0.5 h at room temperature. The resulting mixture was concentrated and the residue was dissolved in AcOEt. The solution was washed with saturated $NaHCO_3$ and saturated NaCl, then dried ($MgSO_4$) and concentrated. The residue was dissolved in $CH_2Cl_2$ (5 mL); then $N^α$-tert-butoxycarbony-$N^{im}$-tosyl-L-histidine (0.48 g, 1.18 mmol), diethyl phosphoryl cyanide ("DEPC") (0.17 mL, 1.18 mmol), and $Et_3N$ (0.19 mL, 1.36 mmol) were added to the solution. This mixture was stirred for 15 h at room temperature, then washed with saturated $NaHCO_3$ and saturated NaCl, dried ($MgSO_4$) and concentrated. The residue was purified by flash chromatography using n-hexane-EtOAc (2:1) as an eluant and crystallized from hexane to give a white powder, III-4 (0.329 g, 58.7%). TLC $R_f$ 0.57 (AcOEt-n-hexane, 1:1); $^1$H-NMR (90 MHz, $CDCl_3$) δ 0.85 (6H, d, J=7 Hz), 0.90 (6H, d, J=7 Hz), 1.05–205 (15H, m), 2.44 (3H, S), 2.96 (2H, brd, J=8 Hz), 3.05–3.40 (3H, m), 3.90–4.45 (3H, m), 5.91 (1H, brd, J=6 Hz), 6.45 (1H, brd, J=8 Hz), 7.10 (1H, s), 7.35 (2H, d, J=9 Hz), 7.80 (2H, d, J=9 Hz), 7.92 (1H, s); MS m/e (M+N+) 620, (M-$C_5H_{10}N_3$) 507. Anal. Calcd. for $C_{29}H_{45}N_7O_6S.\frac{1}{2}$ $CH_2Cl_2$, C, 53.50; H, 6.25; N, 14.81. Found: C, 54.02; H, 6.99; N, 14.42.

e. (4S, 5R, 6S)-4-Azido-5-hydroxy-2,8-dimethyl-6-[$N^α$-(2S-(morpholino-N-carbonyloxy)-3-phenylpropionyl)-$N^{im}$-tosyl-L-histidyl]aminononane (III-5). Compound III-4 (620 mg, 1.00 mmol) was dissolved in TFA (3 mL) and $CH_2Cl_2$ (6 mL), and stirred at room temperature for 1 h. The solution was concentrated and the residue was dissolved in AcOEt, washed with saturated $NaHCO_3$ and saturated NaCl, then dried ($MgSO_4$) and concentraetd. THe residue was dissolved in a solution of (2S)-2-morpholinocarboxy-3-phenyl-1-propionic acid (363 mg, 1.30 mmol; designated compound "II-4" in Scheme II above) in $CH_2Cl_2$ (9 mL). To this mixture was added DEPC (197 μL, 1.30 mmol) and $Et_3N$ (210 μL, 1.50 mmol), with stirring at 0° C. The Reaction mixture was stirred at room temperature for 18 h. After concentration, the residue was dissolved in AcOEt and washed with saturated $NaHCO_3$ and saturated NaCl, then dried ($MgSO_4$) and concentrated. The residue was purified by flash chromatography using n-hexane-AcOEt (1:1) as an eluant to give a white solid, III-5 (630 mg, 80.7%). TLC $R_f$ 0.49 (AcOET-n-hexane, 2:1); $^1$H-NMR (90 MHz, $CDCl_3$) δ 0.60–1.05 (12H, m) 1.05–200 (6H, m), 2.43 (3H, S), 2.70 (1H, brs), 2.80–3.30 (4H, m), 3.30–3.85 (8H, m), 4.05 (1H, brs), 4.55 (1H, brs), 4.95 (1H, brs), 6.45 (1H, brd, J=9 Hz), 7.02 (2H, d, J=8 Hz), 7.22 (5H, s), 7.34 (2H, d, J=8 Hz), 7.65–7.95 (3H, m); MS m/e (M+N+) 781, (N—$C_5H_{10}N_3$) 668. Anal. Calcd. for $C_{38}H_{52}N_8O_8S.\frac{1}{4}$ $CH_2Cl_2$: C, 57.26; H, 6.60; N, 13.97. Found: C, 57.48; H, 6.64; N, 13.22.

f. (4S, 5R, 6S)-4-Azido-5-hydroxy-2,8-dimethyl-6-[$N^α$-(2S-(morpholino-N-carbonyloxy)-3-phenylpropionyl)-L-histidyl]aminononane (III-6). To a stirred solution of III-5 (630 mg, 0.81 mmol) in MeOH (30 mL) was added 1-hydroxybenzotriazole ("HOBt") (327 mg, 2.42 mmol). The stirring was continued for 16 h at room temperature. The reaction mixture was concentrated and the residue was purified by flash chromatography using $CH_2Cl_2$-MeOH (20:1) as an eluant and crystallized in n-hexane to give a white powder, III-6 (425 mg, 80.4%). TLC $R_f$ 0.38 ($CH_2Cl_2$-MeOH, 10:1); $^1$H-NMR (400 MHz, $CDCl_3$) δ 0.78 (3H, d, J=6.0 Hz), 0.81 (3H, d, J=5.9 Hz), 0.96 (3H, d, J=6.6 Hz), 0.97 (3H, d, J=7.6 Hz), 1.10 (1H, m), 1.28 (2H, m), 1.18–1.90 (3H, m), 2.77 (2H, dd, J=14.8, 5.3 Hz), 3.10–3.35 (6H, m), 3.47–3.63 (5H, m), 3.68 (1H, m), 3.78 (1H, m), 4.08 (1H, m), 4.62 (1H, m), 5.03 (1H, dd, J=9.0, 6.4 Hz), 6.50 (1H, d, J=9.3 Hz), 6.83 (1H, s), 7.24–7.35 (5H, m), 7.53 (1H, s), 8.37 (1H, brs); MS m/e (M+H+) 627, (N—$C_5H_{10}N_3$) 514. Anal. Calcd. for $C_{31}H_{40}N_8O_8$: C, 59.40; H, 7.40; N, 17.88. Found: C, 59.60; H, 7.63; N, 17.50.
EXAMPLE 4
This example describes the preparation of (4S, 5R, 6S)-4-azido-7-cyclohexyl-5-hydroxy-2-methyl-6-[N$^\alpha$-(2S-(morpholino-N-carbonyloxy)-3-phenylpropionyl)-L-histidyl]aminoheptane as illustrated in Scheme IV.
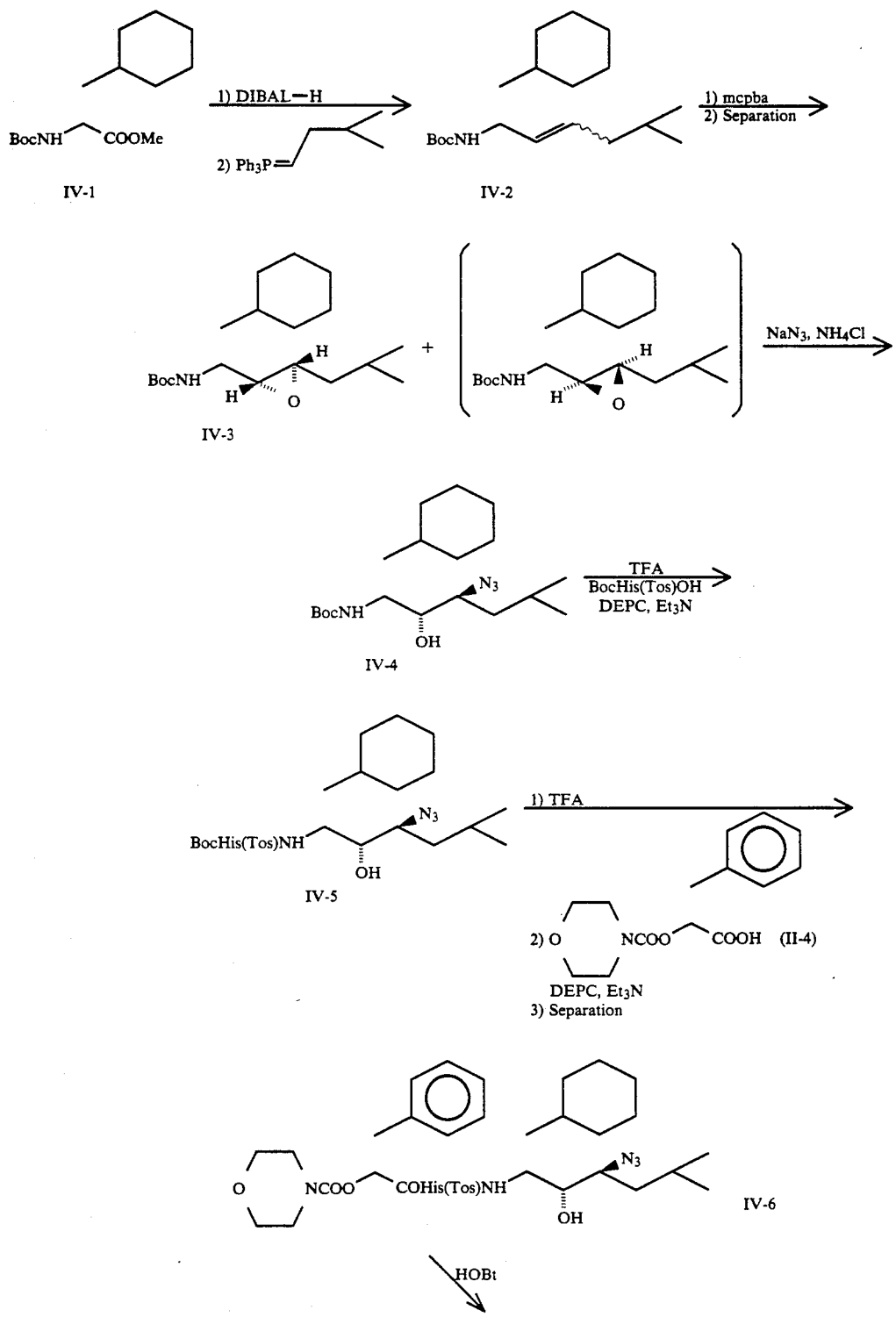

-continued
Scheme IV

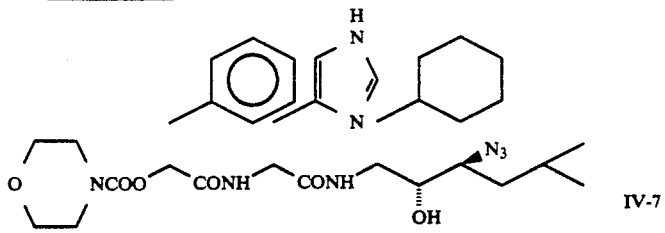

IV-7 a. N-(tert-Butoxycarbonyl)-L-cyclohexylalanine methylester (IV-1). A solution of N-tert-butoxycarbonyl-L-phenylalanine methylester (50 g, 0.179 mol) in MeOH (250 mL) was treated with 5% rhodium on alumina. Hydrogenation was effected at 40~50 psi for 20 h. The catalyst was filtered off and MeOH was evaporated under reduced pressure to dryness to give a colorless oil, IV-1 (50.0 g, 97.8%). $^1$H-NMR (90 MHz, CDCl$_3$) δ 0.73–1.95 (13H, m), 1.50 (9H, s), 3.26 (3H, s), 4.33 (1H, m), 4.85 (1H, brs).

b. Cis and trans mixture of (6S)-6-tert-Butoxycarbonylamino-7-cyclohexyl-2-methyl-hept-4-ene (IV-2). To a stirred −78° C. solution of IV-1 (2.00 g, 7.01 mmol) in toluene (20 mL) was added diisobutylaluminum hydride (1.5M solution in toluene, 6.07 mL, 9.11 mmol). After stirring for an additional 20 min at −78° C., the aldehyde solution was used immediately as described below.

To a stirred 0° C. suspension of isopentyltriphenylphosphonium bromide (4.3 g, 10.50 mmol) in toluene (5 mL) was added potassium bis(trimethylsilyl)amide (0.5M solution in toluene, 21 mL, 10.50 mmol). The mixture was stirred for 1 h at room temperature, then cooled to −78° C. The −78° C. aldehyde solution prepared above was added via cannula. After stirring at −78° C. for 20 min, the mixture was allowed to slowly warm to room temperature and then heated to 40° C. for 20 h. The mixture was then extracted with n-hexane. The extract was washed with H$_2$O and saturated NaCl, then dried (MgSO$_4$) and concentrated. The residue was purified by flash chromatography using n-hexane-AcOEt (20:1) as an eluant to give a colorless oil, IV-2 (0.887 g, 40.9%). TLC R$_f$ 0.62 (AcOET-n-hexane, 1:10); $^1$H-NMR (90 MHz, CDCl$_3$) δ 0.87 (3H, d, J=7 Hz), 0.91 (3H, d, J=7 Hz), 0.99–1.85 (14H, m), 1.45 (9H, s), 2.00 (2H, m), 4.15–4.60 (2H, m), 5.05–5.65 (2H, m); MS m/e (M+H$^+$) 310, (M—C$_7$H$_{13}$) 212. Anal. Calcd. for C$_{19}$H$_{35}$NO$_2$: C, 73.73; H, 11.40; N, 4.53. Found: C, 73.86; H, 11.47; N, 4.43.

c. (4R, 5R, 6S)-6-tert-Butoxycarbonylamino-7-cyclohexyl-4,5-epoxy-2-methyl-heptane (IV-3). To a solution of IV-2 (11.5 g, 37.3 mmol) in CH$_2$Cl$_2$ (30 ml) was added m-chloroperbenzoic acid (80–85%, 12.1 g, 56.1–59.6 mmol) in CH$_2$Cl$_2$ (170 ml). The reaction mixture was stirred at room temperature for 20 h. After concentration, the residue was dissolved in AcOEt and washed with 10% Na$_2$S$_2$O$_3$, saturated NaCl, H$_2$O, and saturated NaCl, then dried (MgSO$_4$) and concentrated. The residue was purified by flash silica gel chromatography using AcOEt-n-hexane (1:20) as an eluant to give IV-3 as a white solid (5.82 g, 47.9%). TLC R$_f$ 0.44 (AcOEt-n-hexane; 1:10); $^1$H-NMR (90 MHz, CDCl$_3$) δ 0.93 (6H, d, J=7Hz), 0.70–1.98 (16H, m), 1.45 (9H, s), 2.70 (1H, dd, J=2, 0.5 Hz), 2.81 (1H, dt, J=2 Hz, 7 Hz), 3.95 (1H, s), 4.33 (1H, m), 4.33 (1H, brd, J=9 Hz); MS m/e: (M+H) 326, (M+H—C$_4$H$_8$) 270.

d. (4S, 5R, 6S)-4-Azido-6tert-butoxycarbonylamino-7-cyclohexyl-5-hydroxy-2-methylheptane (IV-4). A mixed suspension of IV-3 (5.22 g, 16.0 mmol), NaN$_3$ (10.4 g, 160 mmol), and NH$_4$Cl (6.4 g, 120 mmol) in MeOH (200 mL) was heated under reflux with stirring for 2 days. After concentration, the residue was mixed with AcOEt. The resulting mixture was washed with H$_2$O and saturated NaCl, then dried (MgSO$_4$) and concentrated. The residue was purified by flash chromatography using AcOEt-n-hexane (1:15) as an eluant to give a colorless oil, IV-4 (3.35 g, 56.9%). TLC R$_f$ 0.66 (AcOEt-n-hexane, 1:4); $^1$H-NMR (90 MHz, CDCl$_3$) δ 0.96 (3H, d, J=7 Hz), 0.98 (3H, d, J=7 Hz), 1.10–1.40 (7H, m), 1.46 (9H, s), 1.40–1.95 (9H, m), 3.25–3.40 (3H, brm), 3.79 (1H, brs), 4.73 (1H, brd, J=8 Hz); MS m/e (M+H) 369 (M+H—C$_4$H$_8$)313 (M+H—C$_4$H$_8$CO$_2$) 269. Anal. Calcd. for C$_{19}$H$_{36}$N$_4$O$_3$: C, 6192.; H, 9.85; N, 15.20. Found: C, 61.67; H, 9.86; N, 15.42.

e. (4S, 5R, 6S)-4-Azido-6-N$^α$-tert-butoxycarbonyl-N$^{im}$-tosyl-L-histidyl)amino-7-cyclohexyl-5-hydroxy-2-methylheptane (IV-5). To a stirred solution of IV-4 (2.50 g, 6.78 mmol) in CH$_2$Cl$_2$ (12 mL) was added trifluoroacetic acid (6 mL) at 0° C. Stirring was continued for 1 h at room temperature. After concentration, the residue was dissolved in AcOEt and washed with saturated NaHCO$_3$, saturated NaCl, then dried (MgSO4) and concentrated. The residue was dissolved in CH$_2$Cl$_2$ (30 mL), and mixed with N$^α$-tert-butoxycarbonyl-N$^{im}$-tosyl-L-histidine (3.61 g, 8.82 mmol), DEPC (1.34 mL, 8.83 mmol), and Et$_3$N (1.42 mL, 10.19 mmol), with stirring at 0° C. The stirring was continued for 2 h at 0° C. and then for 18 h at room temperature. After concentration, the residue was dissolved in AcOEt and washed with saturated NaHCO$_3$, H$_2$O, and saturated NaCl, then dried (MgSO$_4$) and concentrated. The residue was purified by flash chromatography using AcOEt-n-hexane (1:2) as an eluant to give a colorless oil, IV-5 (3.28 g, 73.2%). TLC R$_f$ 0.69 (AcOEt-n-hexane, 1:1); $^1$H-NMR (400 MHz, CDCl$_3$) δ 0.89 (3H, d, J=6.6 Hz), 0.98 (3H, d, J=6.7 Hz), 1.10~1.50 (7H, m), 1.44 (9H, s), 1.58–1.88 (9H, m), 2.46 (3H, s), 2.99 (2H, m), 3.23 (1H, m), 3.33 (1H, brs), 4.13 (1H, brs), 4.27 (1H, brs), 4.29 (1H, dd, J=11.6, 6.1 Hz), 5.88 (1H, brd, J=5 Hz), 6.34 (1H, brd, J=6 Hz), 7.13 (1H, S), 7.38 (2H, d, J=8.5 Hz), 7.82 (2H, d, J=8.4 Hz), 7.94 (1H, s); MS m/e (M+H$^+$) 660, (M—C$_7$H$_7$O$_2$S+H$_2$) 506. Anal. Calcd. for C$_{32}$H$_{49}$N$_7$O$_6$S: C, 58.25; H, 7.49; N, 14.86; S, 4.86. Found: C, 57.99; H, 7.27; N, 14.88; S, 4.68.

f. (4S, 5R, 6S)-4-Azido-7-cyclohexyl-5-hydroxy-2-methyl-6-[N$^α$-(2S-(morpholino-N-carbonyloxy)-3-phenylpropionyl)-N$^{im}$-tosyl-L-histidyl]aminoheptane (IV-6). Compound IV-5 (3.19 g, 4.83 mmol) was dissolved in a mixed solution of TFA (12 mL) and CH$_2$Cl$_2$ (24 mL) and stirred at room temperature for 1 h. After concentration, the residue was dissolved in AcOEt and washed with saturated NaHCO$_3$ and saturated NaCl, then dried (MgSO₄) and concentrated. The residue was mixed with a solution of compound II-4, (2S)-2-morpholinocarbonyloxy-3-phenylpionic acid (1.76 g, 6.30 mmol) in CH₂Cl₂ (60 mL). To this mixture was added DEPC (0.95 mL, 6.26 mmol) and Et₃N (1.01 mL, 7.25 mmol), with ice-water cooling and stirring. The stirring was continued for 18 h at room temperature. After concentration, the residue was dissolved in AcOET, washed with saturated NaHCO₃, H₂O, and saturated NaCl, then dried (MgSO₄) and concentrated. The residue was purified by flash chromatography using AcO-Et-n-hexane (1:1) as an eluant to give a white powder, IV-6 (2.65 g, 66.8%). TLC $R_f$ 0.43 (CH₂Cl₂—MeOH, 30:1); ¹H-NMR (400 MHz, CDCl₃) δ 0.94 (3H, d, J=6.4 Hz), 0.98 (3H, d, J=6.4 Hz), 1.03–1.33 (6H, m), 1.47–1.90 (10H, m), 2.46 (3H, s), 3.05–3.38 (6H, m), 3.44–3.58 (4H, ). 3.58–3.68 (1H, m), 3.68–3.90 (2H, m), 4.09–4.17 (1H, m), 4.58 (1H, dt, J=6.8, 3.9 Hz), 5.03 (1H, q, J=3.7 Hz), 6.46 (1H, d, J=8.0 Hz), 7.02 (1H, s), 7.19–7.32 (5H, m), 7.39 (2H, d, J=8.2 Hz), 7.76 (1H, d, J=6.9 Hz), 7.82 (1H, d, J=1.8 Hz), 7.83 (2H, d, J=8.3 Hz); MS m/3 (M+H) 821, (M—C₅H₈NO₂+H₂) 708. Anal. Calcd. for C₄₁H₅₆H₈O₈S; C, 59.98; H, 6.88; N, 13.65; S, 3.91. Found: C, 59.45; H, 6.83; N, 13.18; S, 3.42.

g. (4S, 5R, 6S)-4-Azido-7-cyclohexyl-5-hydroxy-2-methyl-6-[N$^\alpha$-(2S-(morpholino-N-carbonyloxy)-3-phenylpropionyl)-L-histidyl]aminoheptane (IV-7). To a stirred solution of IV-6 (2.58 g, 3.14 mmol) n MeOH (110 mL) was added HOBt (1.0 g, 7.40 mmol). The stirring was continued for 20 h at room temperature. After concentration, the residue was purified by flash chromatography using CH₂Cl₂-MeOH (10:1) as an eluant and precipitated from n-hexane to give IV-7 as a white powder, 1.81 g (86.4%). TLC $R_f$ 0.54 (CH₂Cl₂—MeOH, 10:1); ¹H-NMR (400 MHz, CDCl₃) δ 0.96 (3H, d, J=6.8 Hz), 0.98 (3H, d, J=6.9 Hz), 1.03–1.35 (6H, m), 1.44–1.90 (10H, m), 2.78 (1H, dd, J=14.8, 5.0 Hz), 3.12–3.38 (6H, m), 3.46–3.65 (5H, m), 3.65–3.73 (1H, m), 3.73–3.83 (1H, m), 4.09–4.18 (1H, m), 4.58–4.64 (1H, m), 5.14 (1H, dd, J=8.9, 3.5 Hz), 6.49 (1H, d, J=9.1 Hz), 6.84 (1H, s), 7.23–7.35 (5H, m), 7.54 (1H, brs), 8.40 (1H, brs); MS m/e (M+H) 667, (M—C₅H₈NO₂+2H⁺) 554. Anal. Calcd. for C₃₄H₅₀N₈O₈: C, 61.24; H, 7.56; N, 16.81. Found: C, 61.37; H, 7.54; N, 16.53.

EXAMPLE 6

This example describes the preparation of (4S, 5R, 6S)-4-azido-7-cyclohexyl-5-hydroxy-2-methyl-6-[N$^\alpha$-(N-morpholino-N-carbonyl)L-phenylalanyl)-L-histidyl]aminoheptane as illustrated in Scheme V.

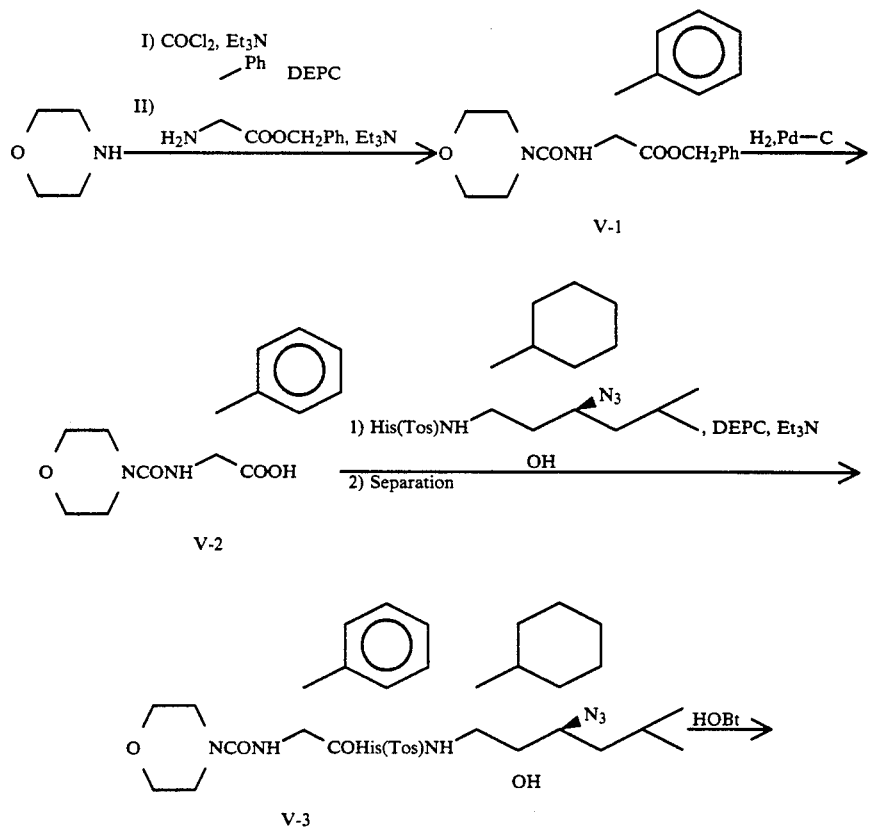

Scheme V

-continued

Scheme V

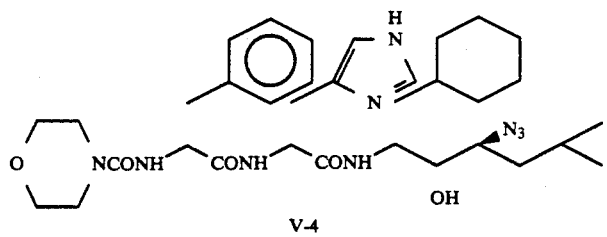

V-4 a. N-(Morpholino-N-carbonyl)-L-phenylalanine Benzylester (V-1). To 20% COCl$_2$ in toluene solution (5.36 mL) was added a solution of morpholine (0.45 mL, 5.16 mmol) and triethylamine (0.64 mL, 4.59 mmol) in CHCl$_3$ (30 mL), with stirring at −30° C. The stirring was continued for 15 min at the same temperature and then for 1 h at room temperature. After concentration, the residue was dissolved in CHCl$_3$ (10 mL) and a solution of L-phenylalanine benzylester [(1.19 g, 4.66 mmol), which was derived by mixing benzyl L-phenylalanine tosylate (2.00 g, 4.67 mmol) and triethylamine (1.92 mL, 13.8 mmol) in CHCl$_3$ (30 mL)] was added, with stirring at 0° C. The mixture was stirred at room temperature for 16 h. After concentration, the residue was dissolved in AcOEt and washed with H$_2$O, saturated NaCl, then dried (MgSO$_4$) and concentrated. The residue was purified by flash chromatography on silica gel using CH$_2$Cl$_2$-MeOH (30:1) as an eluant to give a colorless oil, V11 (1.40 g, 81.9%). TLC R$_f$ 0.82 (CH$_2$Cl$_2$-MeOH, 10:1); $^1$H-NMR (90 MHz, CDCl$_3$) δ 4.05–4.18 (1H, m), 4.29 (4H, t, J=7 Hz), 4.65 (4H, t, J=7 Hz), 5.75–5.90 (1H, m), 5.13 (2H, d, J=2 Hz), 6.90–7.10 (1 H, m), 7.10–7.30 (5H, m), 7.35 (5H, s); MS m/e (M)+ 3.68, (M-C$_7$H$_7$)+ 277, (M-C$_8$H$_7$O$_2$)+ 233.

b. N-(Morpholino-N-carbonyl)-L-phenylalanine (V-2). A solution of V-1 (1.41 g, 3.82 mmol) in MeOH (20 mL) was treated with 10% Pd-C (0.1 g) and stirred under 1 atmosphere of H$_2$ for 2 h. The mixture was filtered and the filtrate was concentrated under reduced pressure to give a colorless oil, V-2 (0.98 g, 92.3%). TLC R$_f$ 0.36 (CHCl$_3$-MeOH-AcOH, 90:10:1); $^1$H-NMR (90 MHz, CDCl$_3$); 3.10–3.40 (6H, m), 3.50–3.75 (4H, m), 4.65 (1H, q, J=7 Hz), 4.92 (1H, d, J=7 Hz), 7.10–7.40 (5H, m); MS m/e (M)+ 278. Anal. Calcd. for C$_{14}$H$_{18}$N$_2$O$_4$ ⅜ CH$_3$OH: C, 58.78; H, 6.95; N, 9.35. Found: C, 58.34; H, 6.33; N, 9.34.

c. (4S, 5R, 6S)-4-Azido-7-cyclohexyl-5-hydroxy-2-methyl-6-[N$^α$-(N-(morpholino-N-carbonyl)L-phenylalanyl)-N$^{im}$-tosyl-L-histidyl]aminoheptane (V-3). (4S, 5R, 6S)-4-azido-6-(N$^α$-tert-butoxycarbonyl-N$^{im}$-tosyl-L-histidyl)-amino-7-cyclohexyl-5-hydroxy-2-methylheptane, IV-5 (0.300 g, 0.46 mmol) was dissolved in a mixed solution of TFA (0.7 mL)-CH$_2$Cl$_2$ (1.5 mL) and the whole solution was then stirred for 1 h at room temperature. After concentration, the residue was dissolved in AcOEt and washed with saturated NaHCO$_3$, H$_2$O, and saturated NaCl, then dried (MgSO$_4$) and concentrated. The residue was dissolved in a solution of compound V-2 N-(morpholinocarbonyl)-L-phenylalanine (0.16 g, 0.57 mmol) in CH$_2$Cl$_2$ (5 mL). The mixture was stirred in an ice-water bath, then DEPC (0.09 mL, 0.59 mmol) and Et$_3$N (0.1 mL, 0.72 mmol) were added. The stirring was continued at room temperature for 18 h. After concentration, the residue was dissolved in AcOEt and was washed with saturated NaHCO$_3$, H$_2$O, and saturated NaCl, then dried (MgSO$_4$) and concentrated. The residue was purified by flash chromatography using CH$_2$CL$_2$-MeOH (30:1) as an eluant and recrystallized from AcOEt-n hexane to give a white solid, V-3 (0.172 g, 45.9%); TLC R$_f$ 0.67 (CH$_2$Cl$_2$-MeOH, 10:1); $^1$H-NMR (400 MHz, CDCl$_3$) δ 0.97 (3H, d, J=6.6 Hz), 0.98 (3H, d, J=6.5 Hz), 1.00–1.30 (5H, m), 1.45–1.75 (10H, m), 1.80–1.91 (1H, m), 2.45 (3H, S), 2.80–2.89 (2H, m), 3.04–3.15 (2H, m), 3.19–3.36 (6H, m), 3.60–3.72 (4H, m), 4.03 (1H, brd, J=11 Hz), 4.17–4.24 (2H, m) 4.65 (2H, dt, J=7.5 Hz, 4.9 Hz), 4.84 (1H, d, J=2.8 Hz), 6.92 (1H, d, J=9.3 Hz), 7.12 (1H, s), 7.22 (2H, d, J=8.1 Hz), 7.25–7.40 (5H, m), 7.82 (2H, d, J=8.5 Hz), 7.83–7.85 (1H, m), 7.98 (1H, d, J=7.3 Hz). Anal. Calcd. for C$_{14}$H$_{57}$N$_9$O$_7$S: C, 60.05; H, 7.01; N, 15.37. Found: C, 59.80; H, 6.90; N, 15.30.

d. (4S, 5R, 6S)-4-Azido-7-cyclohexyl-5-hydroxy-2-methyl-6-[N$^α$-(N-(morpholino-N-carbonyl)L-phenylalanyl)-L-histidyl]aminoheptane (V-4). Compound V-3 (0.159 g, 0.19 mmol) was dissolved in MeOH (7 mL), and HOBt (0.03 g, 0.22 mmol) was added with stirring at room temperature. The stirring was continued for 18 h at the same temperature. After concentration, the residue was purified by flash chromatography using CH$_2$Cl$_2$-MeOH (10:1) as an eluant and recrystallized from EtOAc-n-hexane to give colorless needles, V-4 (0.101 g, 78.2%). TLC R$_f$ 0.49 (CH$_2$Cl$_2$-MeOH, 10:1); $^1$H-NMR (400 MHz, CDCl$_3$) δ 0.80–1.30 (7H, m), 0.98 (3H, d, J=6.5 Hz), 1.00 (3H, d, J=6.5 Hz), 1.40–1.82 (8H, m), 1.82–1.92 (1H, m), 2.83–2.98 (2H, m), 3.07–3.14 (2H, m), 3.14–3.20 (1H, m), 3.24–3.30 (1H, m), 3.32–3.34 (4H, m), 3.60–3.66 (2H, m), 3.66–3.73 (2H, m), 4.10–4.28 (3H, m), 4.65–4.70 (1H, s), 7.26 (2H, d, J=8.4 Hz), 7.31 (1H, t, J=7.1 Hz), 7.38 (1H, t, 7.2 Hz), 7.54 (1H, s), 8.75 (0.6H, brs), 9.50 (0.4H, brs); MS m/e (M-C$_4$H$_8$ON-CONH)+579, (M-C$_4$H$_8$NO-CONH)+536. Anal. Calcd. for C$_{34}$H$_{51}$N$_9$O$_5$.5/4 H$_2$O. C, 59.32; H, 7.84; N, 18.31. Found: C, 59.48; H, 7.62; N, 17.92.

EXAMPLE 6

This example describes the preparation of (4S, 5R, 6S)-4-Azido-6-[N$^α$-(2-benzyl-3-(morpholino-N-carbonyl)propionyl-N$^{im}$-tosyl-L-histidyl]amino-7-cyclohexyl-5-hydroxy-2-methylheptane as illustrated in Scheme VI.

Scheme VI

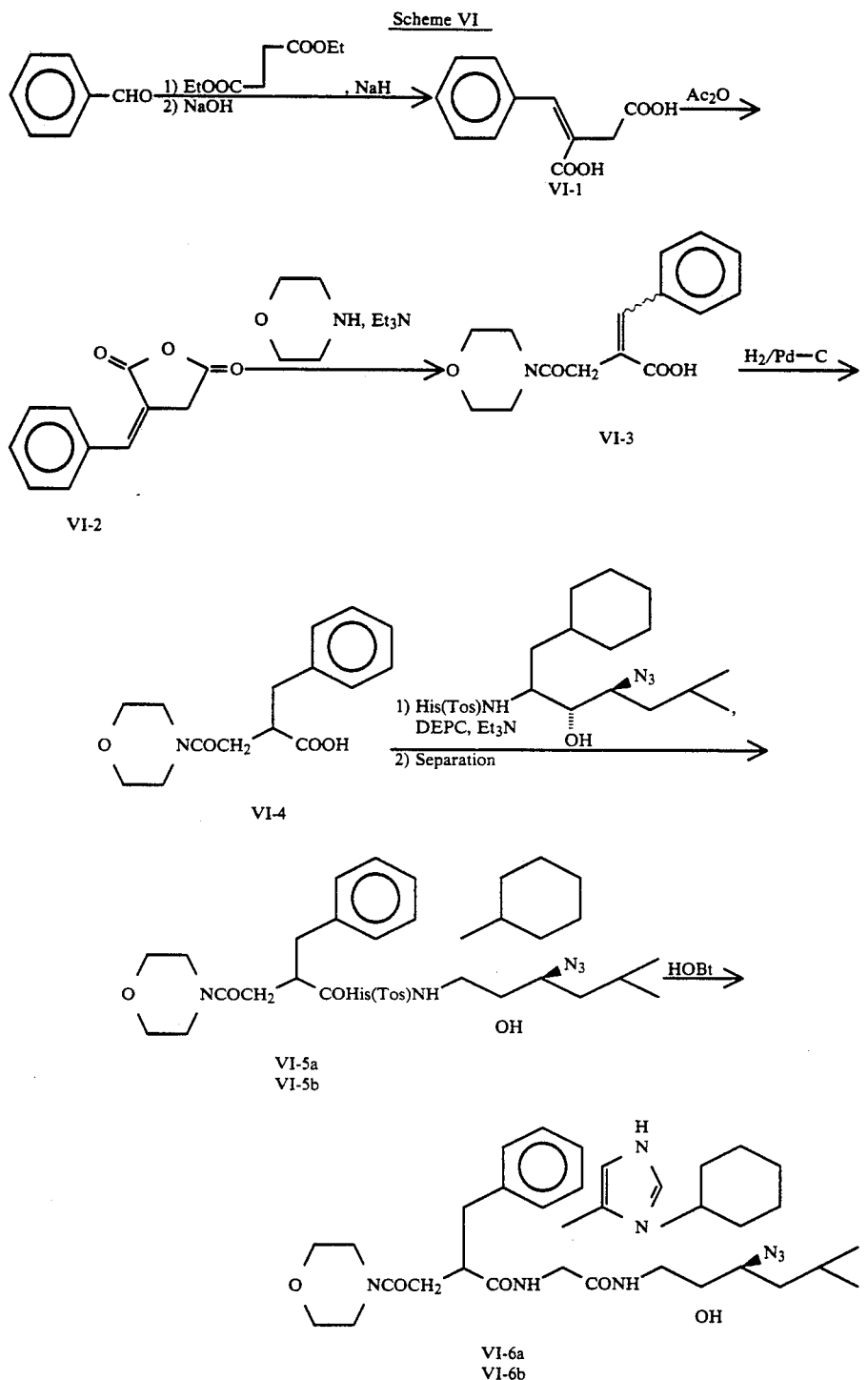

a. 2-Phenylmethylenesuccinic Acid (VI-1). To a stirred solution of benzaldehyde (10.6 g, 0.10 mol) and ethyl succinate (17.4 g, 0.10 mol) in EtOH (150 mL) was added in portions 50% NaH (5.75 g, 0.12 mol) at 0° C. The solution was heated under reflux with stirring for 30 min, then a NaOH aqueous solution [NaOH (4.8 g, 0.12 mol) in H$_2$O (148 mL)] was added and the reaction mixture was heated under reflux with stirring for 1 h. After concentration, the residue was dissolved in H$_2$O and washed with AcOEt. The aqueous layer was acidified with 6N HCl and extracted with AcOEt. The extract was washed with H$_2$O, saturated NaCl, then dried (MgSO$_4$) and concentrated. The reside was recrystallized from AcOEt-n-hexane to give colorless prisms, VI-1 (1.4 g, 6.8%). $^1$H-NMR (90 MHz, DMSO-d$_6$) δ 3.38 (2H, s), 7.42 (5H, s), 7.74 (1H, s), MS m/e (M)$^+$206, (M-CHO$_2$+H)$^+$162. Anal. Calcd. for C$_{11}$H$_{10}$O$_4$. C, 64.08; H, 4.89. Found: C, 63.99; H, 4.63.

b. 2-Phenylmethylenesuccinic Anhydride (VI-2). 2-Phenylmethylenesuccinic acid, VI-1 (0.638 g, 3.09 mmol), was dissolved in Ac$_2$O (20 mL) and heated at 70° C. with stirring for 2 h. After evaporation under reduced pressure, the residue was recrystallized from AcOEt-n-hexane to give a yellow powder, VI-2 (0.320 g, 56.7%). $^1$H-NMR (90 MHz, CDCl$_3$) δ 3.82 (1H, s), 3.85 (1H, s), 7.50 (5H, s), 7.80 (1H, s); MS m/e (M)$^+$188.

c. 2-Phenylmethylene-3-(morpholino-N-carbonyl)-propionic Acid (VI-3). To an ice-cooled stirred solution of 2-phenylmethylenesuccinic anhydride, VI-2 (0.310 g, 1.65 mmol) in CH$_2$Cl$_2$ (15 mL) was added dropwise a solution of morpholine (0.17 mL, 1.95 mmol) and triethylamine in CH$_2$Cl$_2$ (5 mL). The stirring was continued for 2 h at room temperature. After concentration, the residue was dissolved in AcOEt and washed with 1N, HCl, H$_2$O and saturated NaCl, then dried (MgSO$_4$) and concentrated to dryness to give a colorless oil, VI-3 (0.415 g, 91.4%). $^1$H-NMR (90 MHz, CDCl$_3$) δ 3.51 (4H, brs), 2.70 (6H, brs), 6.80 (1H, brs), 7.38 (5H, s), 8.00 (1H, s); MS m/e (M)$^+$375, (M-CHO$_2$+H)$^+$231.

d. (±)-2-Benzyl-3-(morpholino-N-carbonyl)-propionic Acid (VI-4). A solution of VI-3 (0.390 g, 1.42 mmol) in MeOH (15 mL) was treated with 10% Pd-C (0.05 g) and stirred under 1 atmosphere of H$_2$ for 4 h. The mixture was filtered and the filtrate was concentrated. The residue was recrystallized from AcOEt-n-hexane to give colorless needles, VI-4 (0.278 g, 70.5%). $^1$H, NMR (90 MHz, CDCl$_3$) δ 2.40–2.55 (1H, m), 2.60–2.95 (2H, m), 3.00–3.45 (4H, m) 3.45–3.75 (6H, m), 5.95 (1H, brs), 7.25 (5H, s); MS m/e (M)$^+$277. Anal. Calcd. for C$_{15}$H$_{19}$NO$_4$; C, 64.96; H, 6.91; N, 5.05. Found: C, 64.93; H, 6.89; N, 4.86.

e. (4S, 5R, 6S)-4-Azido-6-[N$^α$-(2-benzyl-3-(morpholino-N-carbonyl)propionyl-N$^{im}$-tosyl-L-histidyl]amino-7-cyclohexyl-5-hydroxy-2-methylheptane (VI-5a, VI-5b). (4S, 5R, 6S)-4-Azido-6-(N$^α$-tert butoxycarbonyl-N$^{im}$-tosyl-L-histidyl)amino-7-cyclohexyl-5-hydroxy-2-methylhepane, IV-5 (0.500 g, 0.76 mmol), was dissolved in a mixed solution of TFA (2 mL)-CH$_2$Cl$_2$(2 mL). Then the whole solution was stirred for 1 h at room temperature. After concentration, the residue was dissolved in AcOEt and washed with saturated NaHCO$_3$, H$_2$O, and saturated NaCl, then dried (MgSO$_4$) and concentrated. The residue was dissolved in a solution of compound VI-4 (±)-2-benzyl-3-morpholinocarbonylpropionic acid as prepared in the preceding step (0.27 g, 0.97 mmol) in CH$_2$Cl$_2$ (10 ml). This mixture was stirred in an ice-water bath, then DEPC (0.15 mL) and Et$_3$N (0.1 mL) were added. The stirring was continued in ice-water bath for 2 h. After concentration, the residue was dissolved in AcOEt and washed with saturated NaHCO$_3$, H$_2$O, and saturated NaCl, then dried (MgSO$_4$) and concentrated. The residue was separated by flash silica gel chromatography using CH$_2$Cl$_2$-MeOH (40:1) as an eluant to two isomers: VI-5a (280 mg), VI-5b (167 mg), and mixed oil (112 mg), (total yield: 89.9%).

VI-5a: (oil) TLC R$_f$0.62 (CH$_2$Cl$_2$-MeOH, 20:1 v/v); $^1$H-NMR (400 MHz, CDCl$_3$) δ 0.90 (3H, d, J=6.6 Hz), 0.96 (3H, d, J=6.6 Hz), 1.01–1.70 (15H, m), 1.76–1.85 (1H, m), 2.38–2.47 (2H, m), 2.45 (3H, s), 2.67–2.98 (4H, m), 3.15–3.30 (4H, m), 3.43 (2H, t, J=4.9 Hz), 3.53 (2H, t, J=4.8 Hz), 3.60–3.73 (4H, m), 4.07–4.22 (2H, m), 4.23–4.33 (1H, m), 4.55 (1H, dt, J=7.7 Hz, 4.9 Hz), 6.97 (1H, s), 7.09–7.25 (5H, m), 7.32 (1H, d, J=4.6 Hz), 7.36 (2H, d, J=8.0 Hz), 7.80 (2H, d, J=8.2 Hz), 7.81 (1H, s). Anal. Calcd. for C$_{42}$H$_{58}$N$_8$O$_7$S.CH$_3$OH: C, 60.71; H, 7.29; N, 13.18. Found: C, 61.12; H, 7.25; N, 12.73.

VI-5b: (oil) TLC R$_f$0.53 (CH$_2$Cl$_2$-MeOH, 20:1); $^1$H-NMR (400 MHz, CDCl$_3$) δ 0.90 (3H, d, J=6.6 Hz), 0.97 (3H, d, J=6.6 Hz), 1.05–1.45 (6H, m), 1.45–1.90 (10H, m), 2.44 (3H, s), 2.46–2.54 (1H, m), 2.60–2.65 (1H, m), 2.81–2.90 (2H, m), 2.95 (1H, dd, J=15.7 Hz, 4.9 Hz), 3.09 (1H, dd, J=11.3, 4.2 Hz), 3.14–3.33 (5H, m), 3.49–3.62 (4H, m), 3.62–3.68 (2H, m), 4.09 (1H, m), 4.45 (1H, brs), 4.60 (1H, q, J−5.4 Hz), 6.85 (1H, d, J=9.1 Hz), 7.14 (2H, d, J=8.2 Hz), 7.20 (1H, s), 7.22–7.37 (5H, m), 7.60 (1H, d, J=6.6 Hz), 7.82 (2H, d, J=8.2 Hz), 7.91 (1H, J=1.3 Hz). Anal. Calcd. for C$_{42}$H$_{58}$N$_8$O$_7$S 0.5 CH$_3$OH: C, 61.15; H, 7.19; N, 13.42. Found: C, 61.47; H, 7.19; N, 13.03.

f. (4S, 5R, 6S)-4-Azido-6-[N$^α$-(2-benzyl-3-(morpholino-N-carbonyl)propionyl)-L-histidyl]amino-7-cyclohexyl-5-hydroxy-2-methylheptane (VI-6a, VI-6b). Compounds VI-5a (0.207 g, 0.25 mmol) and VI-5b (0.162 g, 0.20 mmol) were each reacted with HOBt in methanol in a similar manner to that described for the synthesis of V-4 to yield compounds VI-6a and VI-6b, respectively.

VI-6a: 0.0930 g (55.3%): (oil) TLC R$_f$0.52 (CH$_2$Cl$_2$-MeOH, 10:1); $^1$H-NMR (400 MHz, CDCl$_3$) δ 0.92 (3H, d, J=6.6 Hz), 0.97 (3H, d, J=6.6 Hz), 0.85–1.90 (16H, m), 2.30–2.53 (2H, m), 2.73–2.80 (2H, m), 2.86–3.00 (2H, m), 3.04–3.12 (1H, m), 3.17–3.21 (1H, m), 3.24–3.32 (1H, m), 3.43 (2H, m), 3.50 (2H, m), 3.60–3.71 (4H, m), 4.36 (2H, brs), 4.63 (1H, brs), 6.60 (1H, bs), 7.21 (2H, d, J=7.0 Hz), 7.16–7.40 (5H, m), 7.51 (1H, s); MS m/e (M+H)$^+$:665, (M-C$_4$H$_8$NO+H)$^+$, 578. Anal. Calcd. for C$_{35}$H$_{52}$N$_8$O$_5$.0.30 CH$_3$OH: C, 62.98; H, 7.90; N, 16.63. Found: C, 63.41; H, 8.04; N, 16.11.

VI-6b: 0.0964 g (73.6%): oil. TLC R$_f$0.32 (CH$_2$Cl$_2$-MeOH, 10:1) $^1$H-NMR (400 MHz, CDCl$_3$) δ 0.92 (3H, d, J=6.5 Hz), 0.97 (3H, d, J=6.5 Hz), 0.80–1.73 (15H, m), 1.73–1.83 (1H, m), 2.62 (2H, brs), 2.83–3.00 (4H, m), 3.08–3.18 (2H, m), 3.22–3.38 (4H, m), 3.55 (2H, t, J=4.6 H$_2$), 3.61–3.69 (1H, brs), 6.89 (1H, s), 7.18 (2H, d, J=7.0 Hz), 7.24 (1H, t, J=7.7 Hz), 7.32 (3H, t, J=7.6 Hz), 7.56 (1H, s); MS m/e (M+H)$^+$. 665, (M-C$^4$H$_8$NO+H)$^+$578. Anal. Calcd. for C$_{35}$H$_{52}$N$_8$O5·0.5 CH$_3$OH: C, 62.64; H, 7.94; N, 16.47. Found: C, 63.01; H, 8.23; N, 16.26.

EXAMPLE 7

This example describes preparation of 4-azido-7-cyclohexyl-2-methyl-5-oxo-6-[N$^α$-(2S-(morpholino-N-carbonyloxy)-3-phenylpropionyl)-L-histidyl]amino heptane (VII-2).

Scheme VII

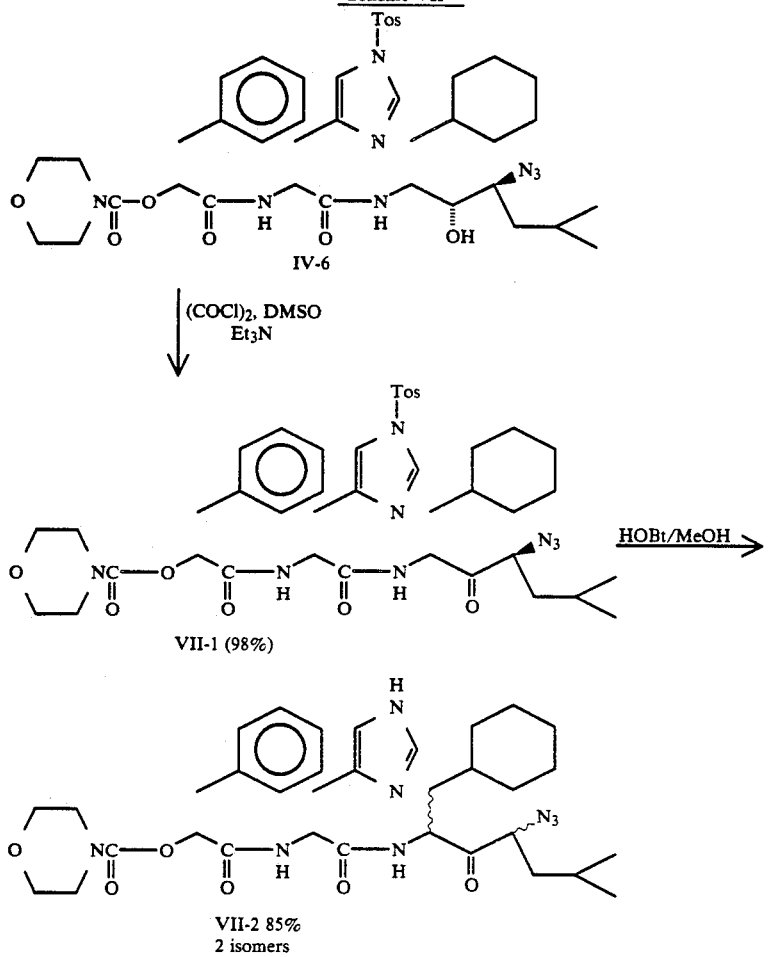

a. (4S, 6S)-4-Azido-7-cyclohexyl-2-methyl-5-oxo-6-[N$^\alpha$-(2S-(morpholino-N-carbonyloxy)-3-phenylpropionyl)-N$^{im}$-tosyl-L-histidyl]amino heptane (VII-1). To a stirred −78° C. solution of oxalyl chloride (0.12 ml, 1.38 mmol) in CH$_2$Cl$_2$ (5ml) under argon was added dimethyl sulfoxide (0.24 ml, 3.38 mmol). After being stirred at −78° C. for 10 min, a solution of (4S, 5R, 6S)-4-Azido-7-cyclohexyl-5-hydroxy-2-methyl-5-oxo-6-[N$^\alpha$-(2S-(morpholino-N-carbonyloxy)-3-phenylpropionyl)-N$^{im}$-tosyl-L-histidyl]aminoheptane (IV-6) (162 mg, 0.197 mmol) in CH$_2$Cl$_2$ (5 ml) was added. The resulting mixture was allowed to stir at −30° to −20° C. for 1 h. To the reaction mixture was added Et$_3$N (0.44 ml, 3.16 mmol). After being stirred at room temperature for 30 min, the reaction mixture was distributed between CH$_2$Cl$_2$ and saturated NaHCO$_3$. The organic phase was washed with brine, dried (MgSO$_4$), and concentrated. The residue was purified by flash chromatography using CH$_2$Cl$_2$-MeOH (50:1) as an eluant to give a white amorphous powder VII-1 (158 mg, 97.9%). R$_f$ 0.64 (CH$_2$Cl$_2$-MeOH, 30:1); $^1$H-NMR (400 MHz, CDCl$_3$): δ 0.74–1.03 (m, 2H), 0.96 (d, J=6.6 Hz, 3H), 0.98 (d, J=6.6 Hz, 3H), 1.06–1.37 (m, 5H), 1.49–1.88 (m, 9H), 2.45 (s, 3H), 2.69 (dd, J=6.1, 15.3 Hz, 1H), 3.04–3.13 (m, 3H), 3.25 (dd, J=4.0, 14.4 Hz, 1H), 3.3014 3.76 (m, 8H), 3.85 (dd, J=4.6, 9.6 Hz, 1H), 4.58 (m, 1H), 4.65 (m, 1H), 5.22 (dd, J=4.1, 7.9 Hz, 1H), 7.08 (s, 1H), 7.16–7.30 (m, 1H), 7.70 (d, J=7.1 Hz, 1H), 7.80–7.85 (m, 3H); $^{13}$C-NMR (400 MHZ, CDCl$_3$): δ 21.46, 21.83, 23.13 (—CH$_3$), 25.27 (—CHMe$_2$), 25.85, 26.12, 26.34, 29.17, 32.03, 33.81, (—CH$_2$—), 34.17 (—CH(CH$_2$)$_5$), 37.77, 38.95 (—CH$_2$—), 44.18, 44.52 (—N—$\underline{\text{CH}}_2$—CH$_2$—O—), 52.01, 54.28, 62.88 (—N—CH—), 66.29, 66.51 (—N—CH$_2$—$\underline{\text{CH}}_2$—O—), 76.07 (—O—CH'—). 114.92, 126.82, 127.32, 127.35, 128.19, 129.30, 130.34, 130.39 (arom $\underline{\text{CH}}$), 134.49, 136.00, 140.33, 146.38, (arom C), 153.96 (N—$\underline{\text{CO}}$—O—), 169.43, 170.10 (—N—$\underline{\text{CO}}$—O—), 205.80 (—C—$\underline{\text{CO}}$—C—); MS (DCI-NH$_3$) m/e 791 (M+H—N$_2$). Anal. Calcd. for C$_{41}$H$_{54}$N$_8$O$_8$S: C, 60.13; H, 6.65; N, 13.68. Found: C, 60.04; H, 6.62; N, 13.81.

b. 4-Azido-7-cyclohexyl-2-methyl-5-oxo-6-[N$^\alpha$-(2S-(morpholino-N-carbonyloxy)-3-phenylpropionyl)-L-histidyl]amino heptane (VII-2). (4S, 6S)-4-Azido-7-cyclohexyl-2-methyl-5-oxo-6-[N$^\alpha$-(2S-(morpholino-N-carbonyloxy)-3-phenylpropionyl)-N$^{im}$-tosyl-L-histidyl]aminoheptane (VII-1) (126 mg, 0.154 mmol) was dissolved in MeOH (5 ml), then HOBt (25 mg, 0.200 mmol) was added with stirring at room temperature. The stirring was continued for 20 h at room temperature. After concentration, the residue was purified by flash chromatography using CH$_2$Cl$_2$-MeOH (20:1) as an eluant to give a white amorphous powder 22 (87 mg, 85.0%). It's a mixture of two isomer. R$_f$ 0.47 and 0.51 (CH$_2$Cl$_2$-MeOH, 10:1); NMR (400 MHz, CDCl$_3$): δ 0.70–1.88 (m, 22H), 2.74–2.87 (m, 1H, 3.08–3.78 (m, 1H), 3.90 (dd, J=4.4, 9.7 Hz, 0.56 H, isomer A) and 4.16 (dd, J=5.4, 8.9 Hz, 0.44 H, isomer B), 4.56–4.71 (m, 2H), 5.10 (dd, J=3.7, 8.8 Hz, 0.44 H, isomer B) and 5.19 (dd, J=3.9, 8.2 Hz, 0.56 H, isomer A), 6.77 (d, J=10.8 Hz, 1H), 7.20–7.64 (m, 8H); MS (DCI-NH$_3$) m/e 637 (M+H−N$_2$). Anal. Calcd. for C$_{34}$H$_{48}$N$_8$O$_6$: C, 61.43; H, 7.28; N, 16.86. Found: C, 61.05; H, 7.21; N, 16.73.

EXAMPLE 8

This example describes preparation of (4S, 5R, 6S)-4-azido-7-cyclohexyl-5-hydroxy-2-methyl-6-[N$^\alpha$-[(E)-2-[(4-morphorinylcarbonyl)methyl]cinnamyl]-L-histidyl]-aminoheptane (VIII-3) as illustrated in Scheme VIII.

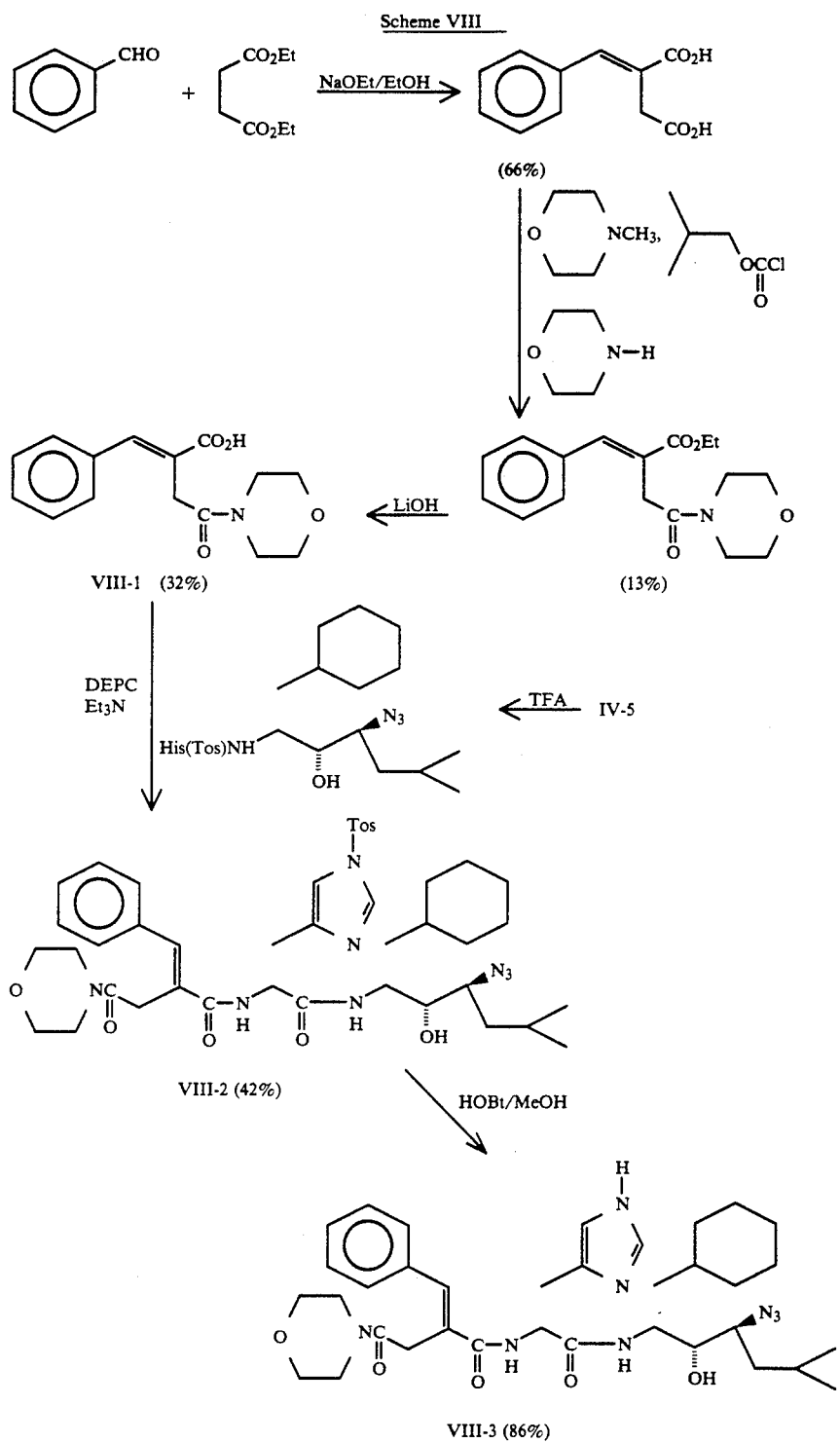

a. (4S, 5R, 6S)-4-Azido-7-cyclohexyl-5-hydroxy-2-methyl-5-hydroxy-6-[N$^\alpha$-[(E)-2-[(4-morphorinylcarbonyl)-methyl]cinnamyl]-N$^{im}$-tosyl-L-histidyl-]aminoheptane (VIII-2) . (4S, 5R, 6S)-4-Azido-7-cyclohexyl-5-hydroxy-2-methyl-6-(N$^\alpha$-tert-butoxycarbonyl-N$^{im}$-tosyl-L-histidyl)amino heptane IV-5(200 mg, 0.303 mmol) was dissolved in TFA (0.5 ml) and CH₂Cl₂ (1 ml), then the mixed solution was stirred for 1 h at room temperature. After concentration, the residue was dissolved in AcOEt and the whole was washed with saturated NaHCO₃ and brine, then dried (MgSO₄) and concentrated. The residue was dissolved in CH₂Cl₂ (3 ml), then to the stirred mixed solution were added (E)-2-[(4-morphorinylcarbonyl)methyl] cinnamic acid (see Plattner et al., *J. Med. Chem.*, 31:2277–2288 (1988) for the synthesis) (108 mg, 0.392 mmol), DEPC (0.060 ml, 0.395 mmol) and Et₃N (0.063 ml, 0.452 mmol) in an ice-water bath. The stirring was continued for 1 h in an ice-water bath, then for 2 h at room temperature. After concentration, the residue was dissolved in AcOEt and the whole was washed with saturated NaHCO₃ and brine, then dried (MgSO₄) and concentrated. The residue was purified by flash column chromatography using AcOEt-n-hexane (2:1) as an eluant to give a white amorphous powder VIII-2 (102 mg, 42.1%). $R_f$ 0.35 (CH₂Cl₂-MeOH, 30:1); NMR (400 MHz, CDCl₃): δ 0.76–1.00 (m, 2H), 0.93 (d, J=6.5 Hz, 3H), 0.97 (d, J=6.7 Hz, 3H), 1.04–1.38 (m, 7H), 1.48–1.88 (m, 7H), 2.44 (S, 3H), 3.03 (dd, J=4.6, 15.0 Hz, 1H), 3.19–3.31 (m, 3H), 3.39–3.78 (m, 11H), 4.06 (bs, 1H), 4.29 (m, 1H), 4.70 (m, 1H), 6.91 (d, J=9.6 Hz, 1H), 7.16–7.45 (m, 9H), 7.82 (td, J=1.9, 8.4 Hz, 2H), 7.93 (d, J=1.3 Hz, 1H), 8.14 (d, J=7.1 Hz, 1H); MS (DCI-NH₃) m/e 817 (M+1). Anal. Calcd. for C₄₂H₅₆N₈O₇S: C, 61.74; H, 6.9; N, 13.72. Found: C, 62.05; H, 7.01; N, 13.66.

b. (4S, 5R, 6S)-4-Azido-7-cyclohexyl-5-hydroxy-2-methyl-6-[N$^α$-[(E)-2-[(4-morphorinylcarbonyl)-methyl]cinnamyl]-L-histidyl]aminoheptane (VIII-3). (4S, 5R, 6S)-4-Azido-7-cyclohexyl-5-hydroxy-2-methyl-6-(N$^α$[(E)-2-[(4-morphorinylcarbonyl)methyl]-cinnamyl]-N$^{im}$-tosyl-L-histidyl)aminoheptane (VIII-2) (89 mg, 0.109 mmol) was dissolved in MeOH (3 ml), then HOBt (18 mg, 0.133 mmol) was added with stirring at room temperature. The stirring was continued for 20 h at room temperature. After concentration, the residue was purified by flash chromatography using CH₂Cl₂-MeOH (20:1) as an eluant to give a white amorphous powder VIII-3 (62 mg, 85.8%). $R_f$ 0.31 (CH₂Cl₂-MeOH, 10:1); NMR (400 MHz, CDCl₃): δ 0.71–1.03 (m, 2H), 0.93 (d, J=6.5 Hz, 3H), 0.97 (d, J=6.6 Hz, 3H), 1.06–1.19 (m, 3H), 1.21–1.91 (m, 13H), 3.05 (dd, J=4.6, 14.8 Hz, 1H), 3.43–3.50 (m, 2H), 3.40 (dd, J=4.8, 14.8 Hz, 1H), 3.43–3.50 (m, 2H), 3.52–3.80 (m, 9H), 4.29 (m, 1H), 4.74 (m, 1H), 6.86 (d, J=9.2 Hz, 1H), 6.92 (S, 1H), 7.21–7.48 (m, 6H), 7.58 (d, J=0.9 Hz, 1H); 8.60 (bs, 1H); MS (DCI-NH₃) m/e 663 (M+H). Anal. Calcd. for C₃₅H₅₀N₈O₅: C, 63,42; H, 7.60; N, 16.91. Found: C, 63.11; H, 7.63; N, 16.64.

EXAMPLE 9

This example describes preparation of (4S, 5R, 6S)-4-azido-7-cyclohexyl-5-hydroxy-2-methyl-6-[N$^α$-[N-(3-amino-3methylbutyryl-L-phenylalanyl]-L-histidyl-]aminoheptane (IX-6) as illustrated in Scheme IX.

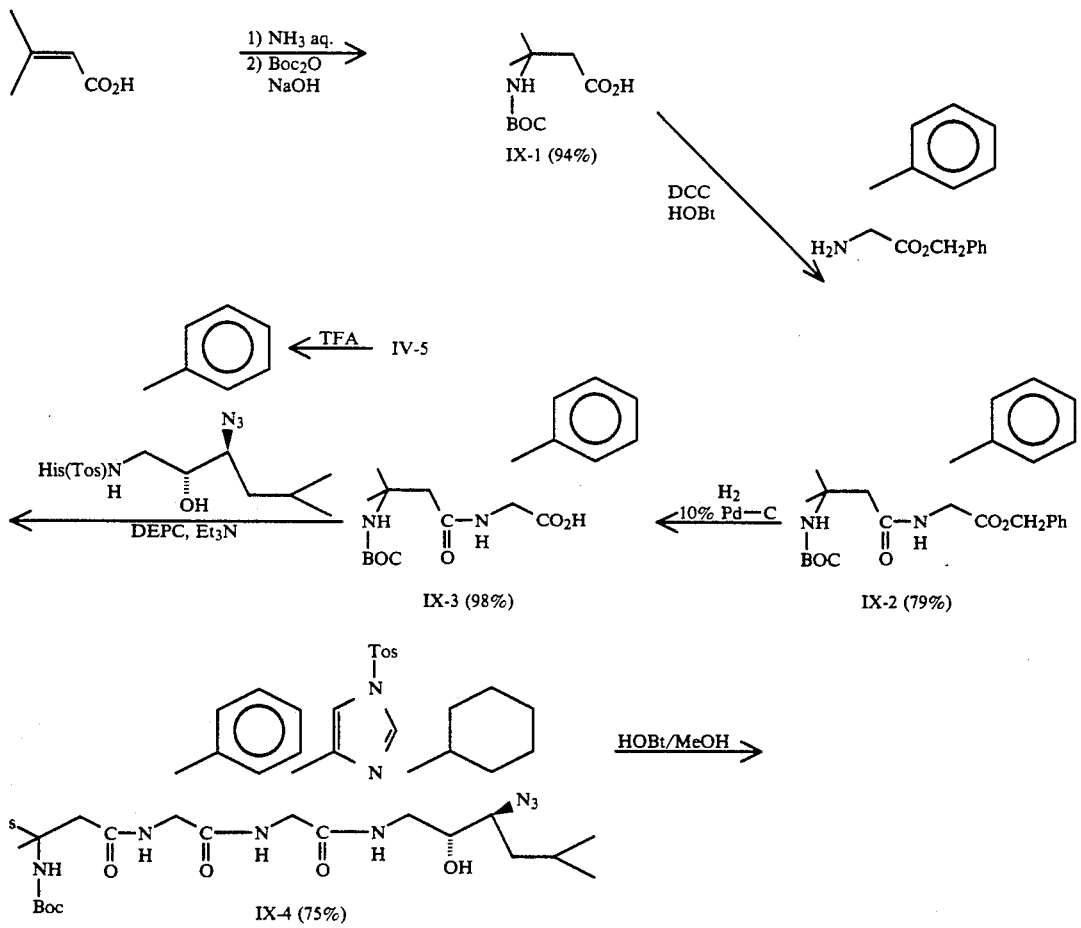

-continued
Scheme IX

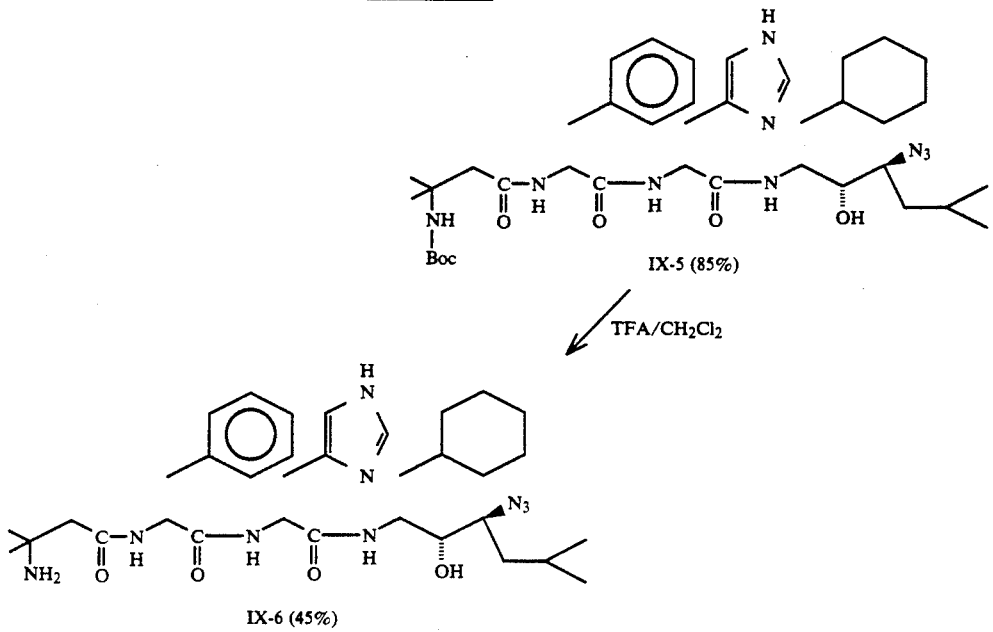

a. 3-tert-Butoxycarbonylamino-3-methylbutyric acid (IX-1), 3,3-Dimethylacrylic acid (2.50 g, 25.0 mmol) in ammonium hydroxide (28.4%, 25 ml) in a sealed steel tube was heated in 160° C. oil bath for 20 h. After cooling, NaOH (1.00 g, 25.0 mmol) was added, then the resulting solution was heated at 100° C. for 2 h. After cooling, dioxane (25 ml) was added, then to the stirred mixed solution was added di-tert-butyl-dicarbonate (6.32 g, 27.5 mmol) in an ice-water bath. The stirring was continued for 20 h at room temperature. After concentration, to the residue was added 1M NaHSO$_4$ solution (30 ml) with cooling, the the whole was extracted with AcOEt (50 ml×2). The organic phase was washed with brine, dried (MgSO$_4$), and concentrated to give a pale yellow oil IX-1 (5.13 g, 94.4%). NMR (90 MHz, CDCl$_3$): δ 1.41 (S, 3H), 1.45 (S, 9H), 1.54 (S, 3H), 2.73 (S, 2H), 5.12 (bs, 1H), MS (DCI-NH$_3$) 218 (M+H).

b. N-(3-tert-butoxycarbonylamino-3-methylbutyryl)-L-phenylalanine benzyl ester (IX-2). L-Phenylalanine benzyl ester p-tosylate (855 mg, 2.0 mmol) was distributed between AcOEt and saturated NaHCO$_3$. The organic phase was washed separately with saturated NaHCO$_3$ and brine. Drying (MgSO$_4$) and evaporating provided a colorless oil (526 mg). This oil was dissolved in DMF (5 ml). To the stirred solution were added a solution of 3-tert-butoxycarbonylamino-3-methylbutyric acid (IX-1) (435 mg, 2.0 mmol) in DMF (3 ml), HOBt (270 mg, 2.0 mmol), and a solution of DCC (418 mg, 2.0 mmol) in DMF (2 ml) at −5° C. The stirring was continued for 3 h at −5° C. then for 16 h at room temperature. The insoluble urea was removed by filtration, and the filtrate was distributed between AcOEt and H$_2$O. The organic phase was washed with saturated NaHCO$_3$ and brine. After drying (MgSO$_4$) and concentration, the residue was purified by flash chromatography using AcOEt-n-hexane (1:2) as an eluant to give a colorless oil IX-2 (716 mg, 78.8%). R$_f$ 0.65 (AcOEt-n-hexane, 1:1); NMR (90 MHz, CDCl$_3$): δ 1.28 (S, 6H), 1.41 (S, 9H), 2.45 and 2.62 (ABq, J=14.6 Hz, 2H), 2.85-3.30 (m, 2H), 4.67-5.05 (m, 2H), 5.08 and 5.21 (ABq, J=10.6 Hz, 2H), 6.13 (bd, J=7.9 Hz, 1H), 6.95-7.45 (m, 10H); MS (DCI-NH$_3$), 455 (M+H).

c. N-(3-tert-butoxycarbonylamino-3-methylbutyryl)-L-phenylalanine (IX-3). A solution of N-(3-tert-butoxycarbonylamino-3-methylbutyryl)-L-phenylalanine benzyl ester (IX-2) (680 mg, 1.50 mmol) in MeOH (15 ml) was treated with 10% Pd-C (68 mg) and stirred under an atmosphere of H$_2$ for 1 h. The mixture was filtrated and the filtrate was concentrated under reduced pressure to give a white solid IX-3 (536 mg, 98.0%). R$_f$ 0.51 (CHCl$_3$-MeOH-AcOH, 90:10:1); NMR (90 MHz, CDCl$_3$+DMSO-d$_6$): δ 1.31 (S, 6H), 1.43 (S, 9H), 2.50 (S, 2H), 2.88-3.39 (m, 2H), 4.84 (m, 1H), 6.35 (bd, J=8.6 Hz, 1H), 7.23 (S, 5H); MS (CDI-NH$_3$) m/e 365 (M+H).

d. (4S, 5R, 6S)-4-Azido-7-cyclohexyl-5-hydroxy-2-methyl-6-[N$^α$-[N-(3-tert-butyloxycarbonylamino-3-methylbutyryl]-L-phenylalanyl]-N$^{im}$-tosyl-L-histidyl]-aminoheptane (IX-4). (4S, 5R, 6S)-4-Azido-7-cyclohexyl-5-hydroxy-2-methyl-6-(N$^α$-tert-butoxycarbonyl-N$^{im}$-tosyl-L-histidyl)aminoheptane (IV-5) (300 mg, 0.455 mmol) was dissolved in TFA (1 ml) and CH$_2$Cl$_2$ (2 ml), then the mixed solution was stirred for 1 h at room temperature. After concentration, the residue was dissolved in AcOEt and the whole was washed with saturated NaHCO$_3$ and brine, then dried (MgSO$_4$) and concentrated. The residue was dissolved in CH$_2$Cl$_2$ (7 ml), then to the stirred mixed solution were added N-(3-tert-butyoxy-carbonylamino-3-methylbutyryl)-L-phenylalanine (IX-3) (215 mg, 0.590 mmol), DEPC (0.090 ml, 0.593 mmol) and Et$_3$N (0.095 ml, 0.682 mmol) in ice-water bath. The stirring was continued for 1 h in an ice-water bath, then for 2 h at room temperature. After concentration, the residue was dissolved in AcOEt and the whole was washed with saturated NaHCO$_3$ and brine, then dried (MgSO$_4$) and concentrated. The residue was purified by flash column chromatography using AcOEt-n-hexane (3:2) as an eluant to give a white amorphous powder IX-4 (308 mg, 74.7%). R$_f$ 0.28 (CH$_2$Cl$_2$-MeOH, 30:1); NMR (400 MHz, CDCl$_3$): δ 0.75-1.00 (m, 3H), 0.95 (d, J=6.6 Hz, 3H), 0.98 (d, J=6.7 Hz, 3H), 1.04–1.38 (m, 6H), 1.18 (S, 3H), 1.31 (S, 3H), 1.42–1.90 (m, 8H), 1.47 (S, 9H), 2.45 (S, 3H), 2.62–2.76 (m, 2H), 2.81 (dd, J=5.1, 14.9 Hz, 1H), 2.86 (dd, J=9.5, 14.3 Hz, 1H), 3.08 (dd, J=5.1, 15.1 Hz, 1H), 3.22–3.32 (m, 3H), 4.06–4.22 (m, 2H), 4.38 (m, 1H), 4.54 (m, 1H), 6.48 (d, J=4.6 Hz, 1H), 6.53 (d, J=9.2 Hz, 1H), 7.12 (S, 1H), 7.18–7.40 (m, 7H), 7.80–7.86 (m, 3H), 7.96 (d, J=1.3 Hz, 1H); MS (DCI-NH₃) m/e 906 (M+H). Anal. Calcd. for C₄₆H₆₇N₉O₈S: C, 60.97; H, 7.45; N, 13.91. Found: C, 61.26; H, 7.58; N, 13.46.

e. (4S, 5R, 6S)-4-Azido-7-cyclohexyl-5-hydroxy-2-methyl-6-[Nα-[N-(3-tert-butoxycarbonylamino-3-methylbutyryl-L-phenylalanyl]-L-histidyl]aminoheptane (IX-5). (4S, 5R, 6S)-4-Azido-7-cyclohexyl-5-hydroxy-2-methyl-6-[Nα-[N-(3-tert-butoxycarbonylamino-3-methylbutyryl)-L-phenylalanyl]-Nⁱᵐ-tosyl-L-histidyl]aminoheptane (IX-4) (249 mg, 0.275 mmol) was dissolved in MeOH (5 ml), then HOBt (56 mg, 0.414 mmol) was added with stirring at room temperature. The stirring was continued for 20 h at room temperature. After concentration, the residue was purified by flash chromatography using CH₂Cl₂-MeOH (15:1) as an eluant to give a white amorphous powder (IX-5) (193 mg, 93.3%). R$_f$ 0.58 (CH₂Cl₂-MeOH, 10:1); NMR (400 MHz, CDCl₃): δ 0.72–1.00 (m, 3H), 0.95 (d, J=6.4 Hz, 3H), 0.98 (d, J=6.6 Hz, 3H), 1.00–1.36 (m, 6H), 1.20 (s, 3H), 1.27 (S, 3H), 1.40–1.82 (m, 8H), 1.48 (S, 9H), 2.59 (d, J=13.3 Hz, 1H), 2.74 (d, J=13.3 Hz, 1H), 2.88 (dd, J=10.0, 14.2 Hz, 1H), 2.91 (dd, J=5.5, 14.6 Hz, 1H), 3.20 (dd, J=4.5, 14.8 Hz, 1H), 3.24–3.29 (m, 2H), 3.33 (dd, J=4.4, 14.3 Hz, 1H), 4.19 (m, 1H), 4.42 (m, 1H), 4.59 (m, 1H), 5.62 (bs, 1H), 6.53 (bs, 1H), 6.60 (bd, J=8.8 Hz, 1H), 6.88 (s, 1H), 7.20–7.38 (m, 5H), 7.60 (S, 1H), 8.04 (bs, 1H); MS (DCI-NH₃) m/e 752 (M+H). Anal. Calcd. for C₃₉H₆₁N₉O₆: C, 62.29; H, 8.18; N, 16.76. Found: C, 62.16; H, 8.25; N, 16.74.

f. (4S, 5R, 6S)-4-Azido-7-cyclohexyl-5-hydroxy-2-methyl-6-[Nα-[N-(3-amino-3-methylbutyryl-L-phenylalanyl]-L-histidyl]aminoheptane (IX-6). (4S, 5R, 6S)-4-Azido-7-cyclohexyl-5-hydroxy-2-methyl-6-[Nα-[N-(3-tert-butoxycarbonyl-amino-3-methylbutyryl)-L-phenylalanyl]-L-histidyl]aminoheptane (IX-5) (21 mg, 0.028 mmol) was dissolved in TFA (0.5 ml) and CH₂Cl₂ (1 ml) at room temperature. The mixed solution was stirred for 1 h at room temperature. After concentration, the residue was purified by preparative reversed-phase HPLC (50×2.2 cm column packed with Vydac 218 TPB 1015 C₁₈ silica, 20–60% CH₃CN/0.1% TFA, linear gradient, 90 min, 15 ml/min). Product fractions were combined and lyophilized to give a white solid IX-6 (11 mg, 45%). HPLC k'=19.45 (20–60% CH₃CN/0.1% TFA, linear gradient, 20 min, 1 ml/min). NMR (400 MHz, CD₃OD): δ 0.92 (d, J=6.6 Hz, 3H), 0.97 (d, J=6.6 Hz, 3H), 1.09 (S, 3H) 1.28 (S, 3H), 1.12–1.93 (m, 13H), 2.37 and 2.47 (ABaq, J=15.4 Hz, 2H), 2.83 (dd, J=11.0, 14.1 Hz, 1H), 3.07 (dd, J=7.7, 15.3 Hz, 1H), 3.13–3.22 (m, 2H), 3.30–3.38 (m, 2H), 4.29 (m, 1H), 4.68 (dd, J=4.3, 10.9 Hz, 1H), 4.73 (dd, J=6.4, 7.8 Hz, 1H), 7.18–7.28 (m, 5H), 7.37 (d, J=1.3 Hz, 1H), 8.78 (d, J=1.3 Hz, 1H); MS (DCI-NH₃) m/e 652 (M+1).

EXAMPLE 10

This example describes the synthesis of (4S, 5R, 6S)-4-azido-7-cyclohexyl-5-hydroxy-2-methyl-6-[Nα-[(S)-2-benzyl-3-(tert-butylsulfonyl)propionyl]-L-histidyl]aminoheptane (X-2b) as illustrated in Scheme X.

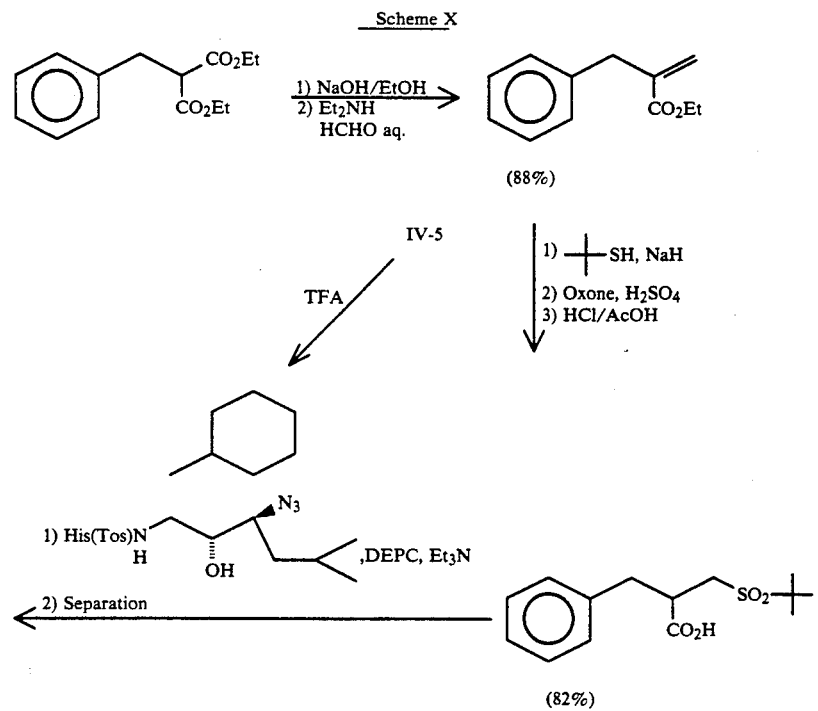

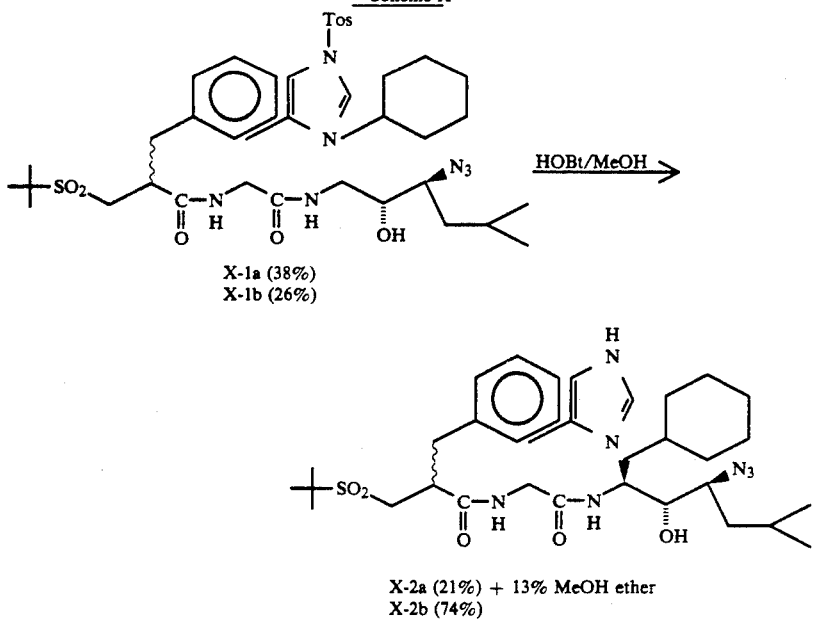

Scheme X

X-1a (38%)
X-1b (26%)

X-2a (21%) + 13% MeOH ether
X-2b (74%)

a. (4S, 5R, 6S)-4-Azido-7-cyclohexyl-5-hydroxy-2-methyl-6-[N$^\alpha$-[2-benzyl-3-(tert-butylsulfonyl)-propionyl]-N$^{im}$-tosyl-L-histidyl]aminoheptane (X-1a, X-1b). (4S, 5R, 6S)-4-Azido-7-cyclohexyl-5-hydroxy-2-methyl-6-(N$^\alpha$-tert-butoxycarbonyl-N$^{im}$-tosyl-L-histidyl)aminoheptane (IV-5) (500 mg, 0.758 mmol) was dissolved in TFA (1 ml) and CH$_2$Cl$_2$ (2 ml), then the mixed solution was stirred for 1 h at room temperature. After concentration, the residue was dissolved in AcOEt and the whole was washed with saturated NaHCO$_3$ and brine, then dried (MgSO$_4$) and concentrated. The residue was dissolved in CH$_2$Cl$_2$ (7 ml), then to the stirred mixed solution were added (+)-2-benzyl-3-(tert-butylsulfonyl) propionic acid (see Bühlmayer et al., *J. Med. Chem.*, 31:1839–1846 (1988) for synthesis) (280 mg, 0.983 mmol). DEPC (0.150 ml, 0.989 mmol) and Et$_3$N (0.158 ml, 1.13 mmol) in an ice-water bath. The stirring was continued for 0.5 h in an ice-water bath, then for 1.5 h at room temperature. After concentration, the residue was dissolved in AcOEt and the whole was washed with saturated NaHCO$_3$ and brine, then drived (MgSO$_4$) and concentrated. The residue was separated by flash column chromatography using AcOEt-n-hexane (2:1) as an eluant to provide 237 mg (37.8%) of X-1a, 164 mg (26.2%) of X-1b, and 67 mg of a mixture of X-1a and X-1b (total yield 74.7%).

X-1a R$_f$ 0.67 (AcOEt-n-hexane, 3:1); NMR (400 MHz, CDCl$_3$): δ 0.66–0.86 (m, 2H), 0.90 (d, J=6.6, 3H), 0.96 (d, J=6.7 Hz, 3H), 0.98–1.72 (m, 13H), 1.42 (s, 9H), 1.74~1.85 (m, 1H), 2.29 (dd, J=4.0, 15.5 Hz, 1H), 2.45 (S, 3H), 2.81 (dd, J=6.4, 13.0 Hz, 1H), 2.90 (dd, J=9.9, 13.0 Hz, 1H), 2.92 (dd, J=1.5, 12.7 Hz, 1H), 3.02 (dd, J=5.7, 15.3 Hz, 1H), 3.11–3.21 (m, 2H), 3.31 (bs, 1H), 3.62 (bs, 1H), 3.77 (dd, J=11.4, 12.5 Hz, 1H), 4.05 (m, 1H), 4.42 (m, 1H), 6.86 (d, J=9.3 Hz, 1H), 6.94 (s, 1H), 7.06 (m, 1H), 7.11–7.19 (m, 4H), 7.37 (d, J=8.0 Hz, 2H), 7.50 (d, J=6.8 Hz, 1H), 7.78 (d, J=1.3 Hz, 1H), 7.81 (td, J=1.9, 8.5 Hz, 2H); MS (DCI-NH$_3$) m/e 826 (M+H). Anal. Calcd. for C$_{41}$H$_{59}$N$_7$O$_7$S$_2$: C, 59.61; H, 7.20; N, 11.87. Found: C, 59.38; H, 7.07; N, 11.56.

X-1b R$_f$ 0.61 (AcOEt-n-hexane, 3:1); NMR (400 MHz, CDCl$_3$): δ 0.79–1.02 (m, 2H), 0.87 (d, J=6.6 Hz, 3H), 0.98 (d, J=6.7 Hz, 3H), 1.08–1.30 (m, 4H), 1.32–1.46 (m, 2H), 1.37 (s, 9H), 1.48–1.86 (m, 9H), 2.45 (s, 3H), 2.86 (dd, J=8.2, 13.5 Hz, 1H), 2.97 (dd, J=2.5, 13.1 Hz, 1H), 3.02–3.09 (m, 3H), 3.14 (m, 1H), 3.28 (dd, J=3.7, 7.7 Hz, 1H), 3.52 (dd, J=9.9, 13.2 Hz, 1H), 4.01 (m, 1H), 4.52 (td, J=5.0, 6.7 Hz, 1H), 6.11 (d, J=8.6 Hz, 1H), 6.78 (d, J=6.8 Hz, 1H), 7.17–7.40 (m, 8H), 7.84 (td, J=1.9, 8.4 Hz, 2H), 7.87 (d, J=1.3 Hz, 1H); MS (DCI-NH$_3$) m/e 826 (M+1). Anal. Calcd. for C$_{41}$H$_{59}$N$_7$O$_7$S$_2$: C, 59.61; H, 7.20; N, 11.87. Found: C, 59.92; H, 7.07; N, 11.61.

b. (4S, 5R, 6S)-4-Azido-7-cyclohexyl-5-hydroxy-2-methyl-6-[N$^\alpha$-[(S)-2-benzyl-3-(tert-butylsulfonyl)-pripionyl]-L-histidyl]aminoheptane (X-2b). (4S, 5R, 6S)-4-Azido-7-cyclohexyl-5-hydroxy-2-methyl-6-[N$^\alpha$-[(S)-2-benzyl-3-(tert-butylsulfonyl)-propionyl]-N$^{im}$-tosyl-L-histidyl]aminoheptane (X-1b) (148 mg, 0.179 mmol) was dissolved in MeOH (5 ml), then HOBt (29 mg, 0.215 mmol) was added with stirring at room temperature. The stirring was continued for 20 h at room temperature. After concentration the residue was purified by flash chromatography using CH$_2$Cl$_2$-MeOH (10:1) as an eluant to give a white powder. This was triturated with AcOEt-n-hexane to give a white powder X-2b (89 mg, 74.0%). R$_f$ 0.31 (CH$_2$Cl$_2$-MeOH, 10:1); NMR (400 MHz, CDCl$_3$): δ 0.79–1.00 (m, 2H), 0.90 (d, J=6.6 Hz, 3H), 0.98 (d, J=6.6 Hz, 3H), 1.12~1.47 (m, 6H), 1.36 (s, 9H), 1.50–1.88 (m, 8H), 2.90 (dd, J=8.0, 13.5 Hz, 1H), 2.96–3.25 (m, 6H), 3.31 (dd, J=3.7, 7.7 Hz, 1H), 3.58 (dd, J=9.8, 13.2 Hz, 1H), 4.04 (m, 1H), 4.53 (m, 1H), 6.30 (d, J=8.7 Hz, 1H), 6.91 (s, 1H), 7.10~7.35 (m, 6H), 7.53 (d, J=0.9 Hz, 1H); MS (DCI-NH$_3$) m/e 672 (m+H). Anal. Calcd. for C$_{34}$H$_{53}$N$_7$O$_5$S: C, 60.78; H, 7.95; N, 14.59. Found: C, 60.50; H, 7.98; N, 14.43.

EXAMPLE 11

This example describes the preparation of (4S, 5R, 6S)-4-azido-7-cyclohexyl-5-hydroxy-2-methyl-6-[N$^\alpha$-[(2R)-2-benzyl-3-[[[2-[(methoxyethoxy)ethyl]methylamino]carbonyl]propionyl]-L-histidyl]aminoheptane (XI-2) as illustrated in Scheme XI.

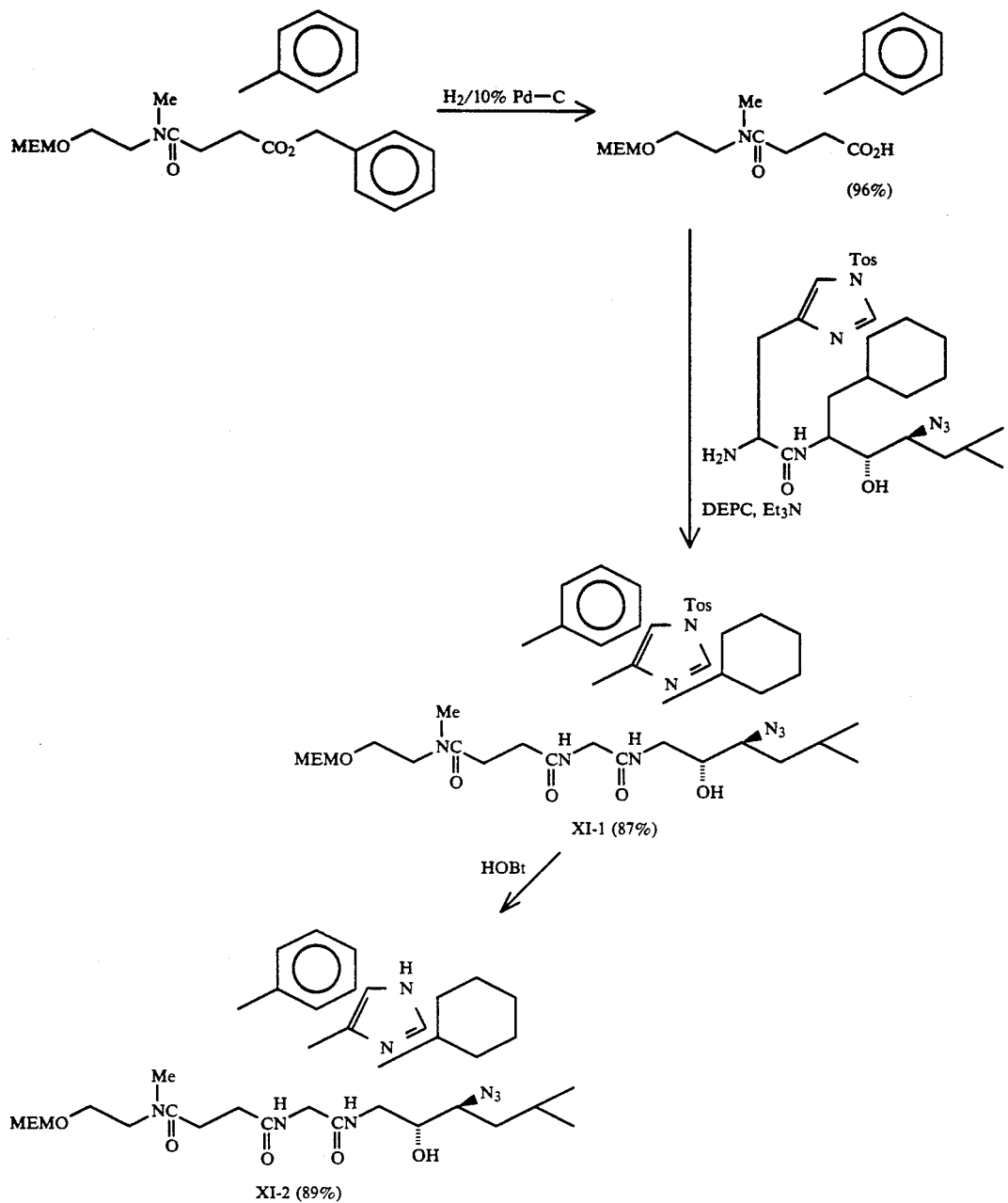

"MEMO" = CH₃OCH₂CH₂OCH₂O— a. (4S, 5R, 6S)-4-Azido-7-cyclohexyl-5-hydroxy-2-methyl-6-(N$^\alpha$-[(2R)-2-benzyl-3-[[[2-[(methoxyethoxy)-methoxy]ethyl]methylamino]carbonyl]propionyl-N$^{im}$-tosyl-L-histidyl]aminoheptane (XI-1). (4S, 5R, 6S)-4-Azido-7-cyclohexyl-5-hydroxy-2-methyl-6-(N$^\alpha$-tert-butyoxycarbonyl-N$^{im}$-tosyl-L-histidyl)aminoheptane (IV-5) (200 mg, 0.303 mmol) was dissolved in TFA (0.5 ml) and CH₂Cl₂ (1.0 ml), then the mixed solution was stirred for 1 h at room temperature. After concentration, the residue was dissolved in AcOEt and the whole was washed with saturated NaHCO₃ and brine, then dried (MgSO₄) and concentrated. The residue was dissolved in CH₂Cl₂ (3 ml), then to the stirred mixed solution were added (2R)-2-benzyl-3-[[[2-[(methoxyethoxy)methoxy]ethyl]-methylamino]carbonyl]propionic acid (see Rosenberg et al., J. Med. Chem., 33:1962-1966 (1990) for synthesis) (139 mg, 0.394 mmol), DEPC (0.060 ml, 0.395 mmol) and Et₃N (0.063 ml, 0.452 mmol) in an ice-water bath. The stirring was continued for 1 h in an ice-water bath, then for 2 h at room temperature. After concentration, the residue was dissolved in AcOEt and the whole was washed with saturated NaHCO₃ and brine, then dried (MgSO₄) and concentrated. The residue was purified by flash column chromatography using AcOEt as an eluant to give a white amorphous powder XI-1 (236 mg, 87.0%). $R_f$ 0.15 (AcOEt-Hexane, 3:1); NMR (400 MHz, CDCl$_3$): δ 0.76–1.88 (m, 16H), 0.906 and 0.910 (2d, J=6.4 Hz, total 3H), 0.96 (d, J=6.6 Hz, 3H), 2.42 (s, 3H), 2.50–3.72 (m, 17H), 2.91 and 2.93 (2S, total 3H), 3.376 and 3.381 (2S, total 3H), 4.09 (m, 1H), 4.44–4.74 (m, 4H), 6.88 and 6.98 (2d, J=8.8 Hz, total 1H), 7.12–7.38 (m, 8H), 7.47 and 7.51 (2d, J=6.8 Hz, total 1H), 7.79–7.84 (m, 2H), 7.90 (d, J=1.1 Hz, 1H); MS (DCI-NH$_3$) m/e 895 (M+H). Anal. Calcd. for C$_{45}$H$_{66}$N$_8$O$_9$S: C, 60:38; H, 7.43; N, 12.52. Found: C, 60.60; H, 7.47; N, 12.75.

b. (4S, 5R, 6S)-4-Azido-7-cyclohexyl-5-hydroxy-2-methyl-6-[N$^\alpha$-[(2R)-2-benzyl-3-[[[2-[(methoxyethoxy)ethyl]methylamino]carbonyl]propionyl]-L-histidyl]aminoheptane (XI-2). (4S, 5R, 6S)-4-Azido-7-cyclohexyl-5-hydroxy-2-methyl-6-[N$^\alpha$-[(2R)-2-benzyl-3-[[[2-[(methoxyethoxy)methoxy]ethyl]methylamino]-carbonyl]propionyl]-N$^{im}$-tosyl-L-histidyl]aminoheptane (XI-1) (219 mg, 0.245 mmol) was dissolved in MeOH (10 ml), then HOBt (40 mg, 0.294 mmol) was added with stirring at room temperature. The stirring was continued for 20 h at room temperature. After concentration, the residue was purified by flash chromatography using CH$_2$Cl$_2$-MeOH (20:1→10:1) as an eluant to give a white amorphous powder XI-2 (161 mg, 88.7%). $R_f$ 0.30 (CH$_2$Cl$_2$-MeOH, 10:1); NMR (400 MHz, CDCl$_3$): δ 0.75–0.92 (m, 2H), 0.93–0.99 (m, 6H), 1.10–1.89 (m, 14H), 2.53 (dd, J=17Hz, 3.3 Hz, 1H), 2.69–3.02 (m, 5H), 2.91 and 3.00 (2S, total 3H), 3.04–3.72 (m, 13H), 3.39 and 3.40 (2S, total 3H), 4.02 (bs, 1H), 4.54–4.74 (m, 4H), 6.54 and 6.66 (2bs, total 1H), 6.87 (d, J=5.3 Hz, 1H), 7.18–7.34 (m, 5H), 7.55–7.57 (m, 1H); MS (DCI-NH$_3$) m/e 741 (M+H). Anal. Calcd. for C$_{38}$H$_{60}$N$_8$O$_7$: C, 61.60; H, 8.16; N, 15.12. Found: C, 61.82; H, 7.90; N, 14.96.

EXAMPLE 12 a. Human Renin Enzyme Assay. The human renin enzyme assay described by Sham et al., *J. Med. Chem.* 31:284–295 (1988) was carried out by mixing 0.24 mGU human kidney renin, 0.21 αμM of angiotensinogen in 0.135 M, pH 6.0, maleate buffer containing 3 mM EDTA, 1.4 mM PMSF, and 0.44% BSA. The total assay volume was 100 μl. All inhibitors were dissolved in DMSO first and diluted with 0.5% BSA to give the appropriate concentrations for testing. The final DMSO concentration in the assay mixture was kept constant at 1%. This concentration of DMSO did not interfere with the enzyme assay. For assay, 90 μl of the above-mentioned maleate buffer containing the renin and inhibitor was preincubated at 37° C. for 5 min and the reaction was continued for 10 additional min after adding 10 μl of substrate. The reaction was stopped by immersion of all tubes in a dry ice acetone-methanol bath. All samples were thawed to 0.4° C. and an aliquot from each tube was taken for the Angiotensin I RIA assay.

b. Angiotensin I Radioimmunoassay. A 100 μl portions of 5% BSA containing a small aliquot of the above enzyme mixture was mixed with 100 μl of angiotensin I [$^{125}$I] (500 mCi/mg) in 0.1M Tris-acetate buffer, pH 7.4 (one part angiotensin I in 50 parts buffer), and 500 μl of antiserum (the lyophilized powder was reconstituted with 125 ml of 0.1M Tris-acetate buffer, pH 7.4). The mixture was incubated at 4° C. for 18 to 24 h. At the end of the incubation, 1.0 mL of charcoal suspension (600 mg of charcoal in 50 mL of 0.1M Tris-acetate buffer, pH 7.4) was pipetted into each tube. The charcoal suspension was stirred constantly during the transfer. The samples were mixed and then centrifuged at 3000×g for 15 min. The supernatants were transferred into properly numbered tubed for gamma counting.

A reagent blank was carried out with each assay. The blank tube contained 100 μl of 5% bovine serum albumin (BSA), 100 μl of angiotensin I [$^{125}$I], and 500 μl of 0.1M Tris-acetate buffer.

A standard curve was prepared with each set of experiments by mixing various amounts (5 to 0.1 ng/ml) of angiotensin I in 0.1M Tris-acetate buffer containing 5% BSA and the same amounts of $^{125}$I-angiotensin I and antiserum as for the RIA assay. The tubes containing the standards were treated exactly like those containing the samples. The amount of angiotensin I produced by the enzyme in each sample was calculated using an angiotensin I standard curve.

The whole process of RIA was carried out at 0° to 4° C. to avoid deterioration of antiserum and angiotensin I. Only polystyrene tubes were used. Polystyrene tubes had shown no affinity for antibody under the assay conditions described above.

An IC$_{50}$ was calculated for each inhibitor tested by conducting the assay in the presence of different concentrations of inhibitor. The inhibitor concentration that caused a 50% reduction in the release of angiotensin I when compared to control (no inhibitor) values was then calculated.

c. Enzyme Kinetics Assay. The determination of K$_m$ and V$_{max}$ was made by using a wide range of substrate concentrations (0.1–1.0 μM). A corresponding set of renin-free blanks was set up simultaneously. The assay was carried out exactly as described above, but no inhibitor was added. By using the Lineweaver-Burke plot, K$_m$ and V$_{max}$ were obtained. For all renin inhibitors having an IC$_{50}$ value below 10 μM, K$_i$ values were calculated using the following equation: K$_i$=IC$_{50}$/(1+[S]/km); [S]=substrate concentration.

IC$_{50}$ values are given in Table 1.

TABLE 1

| Compound No. | IC$_{50}$ (nM) |
|---|---|
| I-5b | 190 |
| III-6 | 110 |
| IV-7 | 1.7 |
| V-4 | 0.58 |
| VI-6b | 0.64 |
| VII-2 | 5.1 |
| VIII-3 | 0.85 |
| IX-6 | 5.4 |
| X-2b | 0.006 |
| XI-2 | 0.008 | b. In vivo efficacy: Oral activity of a number of the compounds of the invention was established by administration to Cynomolgus monkeys, a species known to be susceptible to the antihypertensive effect of renin inhibition. Two male monkeys, young adults approximately 3–6 kg at dosing, were tested over a six-week period. The animal room environment and photoperiod were controlled (temperature approximately 24° C., humidity 50±20%, 12 h light, 12 h dark), as was diet (low salt primate chow, plus discretionary supplements of fruit for at least 7 days prior to dosing). A diuretic (furosemide 1 mg/kg) was given daily by intravenous injection for 7 days prior to dosing.

The compounds of the invention were dissolved in 0.02 N HCl and prepared to the appropriate volume with sterile water. The pH of the solutions were adjusted to approximately 4.0 with 0.02 N NaOH. The solutions were then given orally by an oesophageal gavage at a dose level of 1.0 mg/kg, and a dose volume of 2 mL/kg body weight.

Prior to and following dosing, the animals were connected to an ECG and blood pressure monitor. Systolic, diastolic and mean blood pressure as well as heart rate were measured at 30 second intervals and recorded. Reduction in blood pressure was seen within approximately 1 to 6 hours with all of the compounds tested, including compounds IV-7 and X-2b.

We claim:

1. A renin inhibiting compound having the structural formula

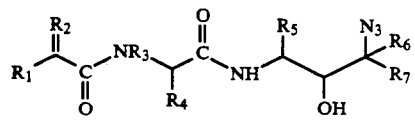

wherein:
- $R_1$ is selected from the group consisting of hydrogen, lower alkyl, lower oxyalkyl containing 1 to 3 oxygen atoms, $-R_{1b}-(CO)-R_{1a}$, and $R_{1b}-(SO_2)-R_{1a}$, where $R_{1b}$ is NH, lower alkyl-substituted amino, S, O, $CH_2$ or CHOH, and $R_{1a}$ is lower alkyl, lower oxyalkyl containing 1 to 3 oxygen atoms, cycloalkyl, lower alkenyl, aryl of 1 to 2 rings, alkoxy, alkenyloxy, hydroxyalkoxy, dihydroxyalkoxy, aminoalkyl, N-protected aminoalkyl, or amino $NR_{1c}R_{1d}$ where $R_{1c}$ and $R_{1d}$ are independently selected from the group consisting of hydrogen, lower alkyl and lower oxyalkyl containing 1 to 3 oxygen atoms, or are linked together to form a piperidino or morpholino ring;
- $R_2$ is selected from the group consisting of lower alkyl, cycloalkyl methyl, benzyl, halobenzyl, lower alkyl-substituted benzyl, lower alkoxy-substituted benzyl, amino-substituted benzyl, naphthyl, halonaphthyl, lower alkyl-substituted naphthyl, lower alkoxy-substituted naphthyl, amino-substituted naphthyl, phenethyl, phenoxy, thiophenoxy, and anilino;
- $R_3$ is hydrogen or lower alkyl;
- $R_4$ is selected from the group consisting of lower alkyl, lower alkenyl, alkoxy-substituted lower alkenyl, lower alkoxy, benzyl, and N-, O- and/or S-containing heterocyclic ring substituted methyl;
- $R_5$ is selected from the group consisting of lower alkyl, cycloalkyl methyl, and benzyl;
- $R_6$ is selected from the group consisting of hydrogen, lower alkyl, vinyl and arylalkyl; and
- $R_7$ is selected from the group consisting of hydrogen and lower alkyl, and pharmaceutically acceptable salts and esters thereof.

2. A renin inhibiting compound having the structural formula

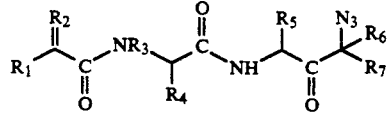

wherein:
- $R_1$ is selected from the group consisting of hydrogen, lower alkyl, lower oxyalkyl containing 1 to 3 oxygen atoms, $-R_{1b}-(CO)-R_{1a}$, and $R_{1b}-(SO_2)-R_{1a}$, where $R_{1b}$ is NH, lower alkyl-substituted amino, S, O, $CH_2$ or CHOH, and $R_{1a}$ is lower alkyl, lower oxyalkyl containing 1 to 3 oxygen atoms, cycloalkyl, lower alkenyl, aryl of 1 to 2 rings, alkoxy, alkenyloxy, hydroxyalkoxy, dihydroxyalkoxy, aminoalkyl, N-protected aminoalkyl, or amino $NR_{1c}R_{1d}$ where $R_{1c}$ and $R_{1d}$ are independently selected from the group consisting of hydrogen, lower alkyl and lower oxyalkyl containing 1 to 3 oxygen atoms, or are linked together to form a piperidino or morpholino ring;
- $R_2$ is selected from the group consisting of lower alkyl, cycloalkyl methyl, benzyl, halobenzyl, lower alkyl-substituted benzyl, lower alkoxy-substituted benzyl, amino-substituted benzyl, naphthyl, halonaphthyl, lower alkyl-substituted naphthyl, lower alkoxy-substituted naphthyl, amino-substituted naphthyl, phenethyl, phenoxy, thiophenoxy, and anilino;
- $R_3$ is hydrogen or lower alkyl;
- $R_4$ is selected from the group consisting of lower alkyl, lower alkenyl, alkoxy-substituted lower alkenyl, lower alkoxy, benzyl, and N-, O- and/or S-containing heterocyclic ring substituted methyl;
- $R_5$ is selected from the group consisting of lower alkyl, cycloalkyl methyl, and benzyl;
- $R_6$ is selected from the group consisting of hydrogen, lower alkyl, vinyl and arylalkyl; and
- $R_7$ is selected from the group consisting of hydrogen and lower alkyl, and pharmaceutically acceptable salts and esters thereof.

3. (4S, 5R, 6S)-4-azido-7-cyclohexyl-5-hydroxy-2-methyl-6-[$N^\alpha$-[(S)-2-benzyl-3-(tert-butylsulfonyl)propionyl]-L-histidyl]aminoheptane.

4. (4S, 5R, 6S)-4-azido-7-cyclohexyl-5-hydroxy-2-methyl-6-[$N^\alpha$-[(2R)-2-benzyl-3-[[2-[methoxyethoxy)ethyl]methylamino]carbonyl]pripionyl]-L-histidyl-]aminoheptane.

* * * * *